(12) United States Patent
Suzuki et al.

(10) Patent No.: US 6,336,354 B1
(45) Date of Patent: Jan. 8, 2002

(54) GAS CONCENTRATION MEASURING APPARATUS COMPENSATING FOR ERROR COMPONENT OF OUTPUT SIGNAL

(75) Inventors: Toshiyuki Suzuki, Handa; Eiichi Kurokawa, Okazaki; Tomoo Kawase, Aichi-ken; Satoshi Hada, Kariya, all of (JP)

(73) Assignee: Denso Corporation, Tokyo (JP)

( * ) Notice: Subject to any disclaimer, the term of this patent is extended or adjusted under 35 U.S.C. 154(b) by 0 days.

(21) Appl. No.: 09/497,179

(22) Filed: Feb. 3, 2000

(30) Foreign Application Priority Data

Feb. 3, 1999 (JP) .............................. 11-026062

(51) Int. Cl.⁷ ..................... G01N 27/12; G01N 37/00; G01N 7/00
(52) U.S. Cl. ................. 73/31.05; 73/23.21; 73/1.06; 422/98; 422/94; 338/34
(58) Field of Search ............................ 73/31.05, 31.03, 73/23.23, 23.21, 23.2, 335.03, 335.04, 335.05, 1.06; 204/424, 431; 338/34; 422/94, 98

(56) References Cited

U.S. PATENT DOCUMENTS

| 3,727,450 A | * | 4/1973 | Luckers ........................ 73/23 |
| 4,291,572 A | * | 9/1981 | Maurer et al. ................. 73/23 |
| 4,620,437 A | * | 11/1986 | Tatrami et al. ................ 73/23 |
| 5,062,065 A | * | 10/1991 | Lampe .................... 364/571.04 |
| 5,467,651 A | * | 11/1995 | Manatra .................... 73/23.21 |
| 5,668,304 A | * | 9/1997 | Kelleter et al. ............. 73/31.05 |
| 5,672,811 A | | 9/1997 | Kato et al. .................. 73/31.05 |
| 5,686,654 A | * | 11/1997 | Friese et al. ............... 73/23.32 |
| 5,698,771 A | * | 12/1997 | Shields et al. ............. 73/31.05 |
| 5,780,715 A | * | 7/1998 | Imblum ...................... 73/23.21 |
| 5,808,461 A | * | 9/1998 | Weigold et al. ............. 324/71.1 |
| 5,844,122 A | * | 12/1998 | Kato ........................... 73/1.06 |
| 5,852,228 A | * | 12/1998 | Yamashita et al. ......... 73/23.32 |
| 6,082,176 A | * | 7/2000 | Kondo et al. ............... 73/23.31 |

FOREIGN PATENT DOCUMENTS

JP          08-271476          10/1996

* cited by examiner

Primary Examiner—Hezron Williams
Assistant Examiner—David Wiggins
(74) Attorney, Agent, or Firm—Pillsbury Winthrop LLP

(57) ABSTRACT

A gas concentration measuring apparatus is provided which measures the concentration of a given gas using a gas sensor. The gas sensor includes a sensor element producing a gas concentration signal indicative of the concentration of the gas, a heater heating the sensor element, and an insulator disposed between the sensor element and the heater. The apparatus includes a heater control circuit which may provisionally supply electrical power to the heater by applying a Pulse-Width-Modulated signal. The heater control circuit performs a switching operation to supply power to the heater cyclically. The apparatus corrects an error contained in the gas concentration signal arising from a leakage current flowing into the sensor element through the insulator during the switching operation of the heater control circuit.

27 Claims, 19 Drawing Sheets

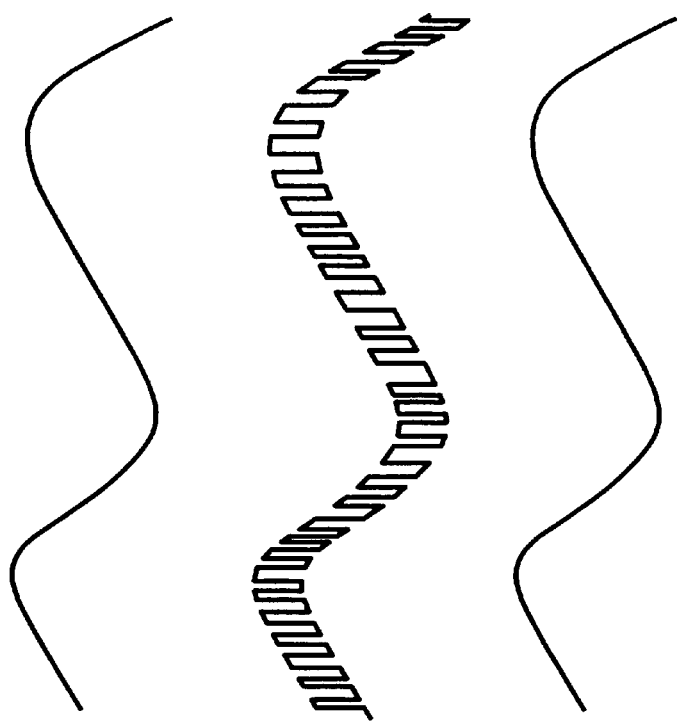
FIG. 12(a) NOx CON. CHANGE
FIG. 12(b) NOx CON. CHANGE CONTAINING LEAKAGE CURRENT ERROR
FIG. 12(c) WAVEFORM OF SIGNAL AFTER PASSING THROUGH LPF

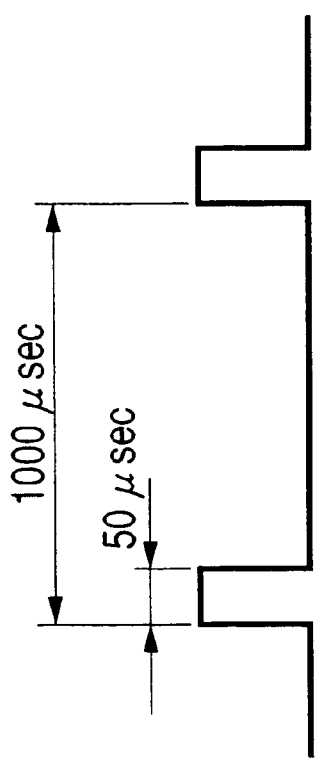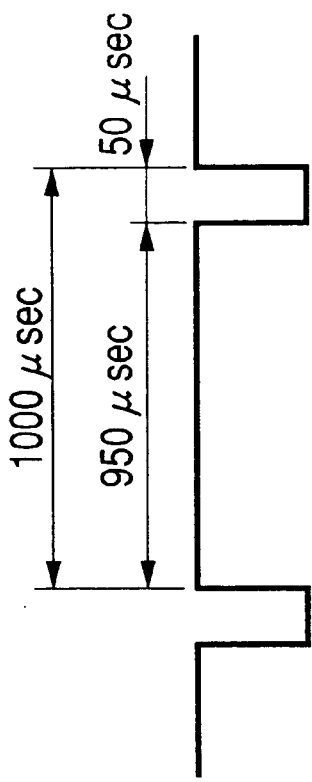
FIG. 13(a)  FREQUENCY=1kHz  DUTY CYCL=5%
FIG. 13(b)  FREQUENCY=1kHz  DUTY CYCL=95%

FIG. 16(a)
HEATER CONTROL SIGNAL (ON-OFF SIGNAL)
FIG. 16(b)
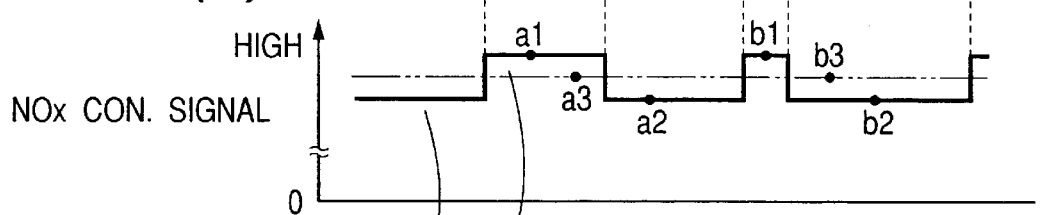
NOx CON. SIGNAL
FIG. 16(c)
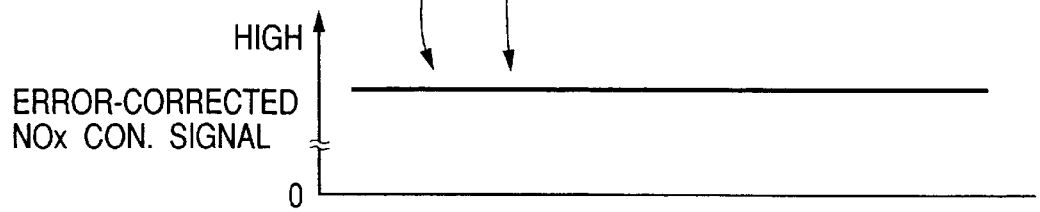
ERROR-CORRECTED NOx CON. SIGNAL

GAS CONCENTRATION MEASURING APPARATUS COMPENSATING FOR ERROR COMPONENT OF OUTPUT SIGNAL

BACKGROUND OF THE INVENTION

1. Technical Field of the Invention

The present invention relates generally to a gas concentration measuring apparatus for measuring the concentration of gases which may be employed in an air-fuel ratio control system for automotive vehicles, and more particularly to a gas concentration measuring apparatus designed to correct an error contained in an output of a gas concentration sensor.

2. Background Art

The air pollution caused by exhaust emissions of automotive internal combustion engines is giving rise to a serious problem at the present day. The exhaust emission control standard regulations have been made more rigorous recently. The burning control of gasoline or diesel engines or use of catalyst are, therefore, being studied to reduce pollutants contained in exhaust gasses. In U.S., OBD-II (On Board Diagnostic-II) requirements prescribe that automotive vehicles have a function of determining whether a catalytic converter is operating normally or not.

As one of systems meeting the OBD-II requirements, a two-$O_2$ sensor monitoring system is proposed which monitors outputs of two $O_2$ sensors mounted upstream and downstream of a catalytic converter, respectively, but it is not designed to detect pollutants directly and cannot determine whether pollutants in exhaust gasses have been reduced accurately or not.

If it becomes possible to measure the concentration of NOx in exhaust gasses for monitoring the burning control and the catalytic converter, the pollutants in the exhaust gasses can be reduced greatly. Specifically, the reduction in pollutants in exhaust emissions of the engine is achieved by controlling the quantity of fuel to be injected into the engine and the EGR rate based on the concentration of NOx contained in the exhaust gasses. Additionally, the determination of deterioration of the catalytic converter is achieved easily by installing a NOx sensor downstream of the catalytic converter.

NOx sensors capable of measuring the concentration of NOx accurately and techniques for mounting such NOx sensors in automotive vehicles are, therefore, being sought.

The effects of air-fuel ratio feedback control may be improved further by monitoring the concentration of $O_2$ contained in the exhaust gasses as well as the concentration of NOx. Specifically, modern air-fuel ratio control for automotive vehicles is required to improve the accuracy of the control and perform lean burn engine control. For meeting these requirements, sensors capable of determining the air-fuel ratio of a mixture supplied to the engine over a wide range are preferable.

Keeping such sensors activated to maintain the accuracy of detection at a certain level requires a heater for keeping the temperature of the sensor at a constant value required for activation of the sensor. The heater may be built in the sensor. In this case, an insulator is disposed between the heater and a sensor element of the sensor. A supply of power to the heater is controlled cyclically by turning on and off a switch connecting a power supply and the heater. An increase in temperature of the sensor element by the heater, however, causes the resistance of the insulator of the sensor to drop, which will cause a leakage current to flow to the sensor element through the insulator during on-off control of the supply of power to the heater, resulting in addition of an error current to an output of the sensor element. Even if the resistance of the insulator is constant, an increase in voltage applied to the heater during the on-off control of the supply of power to the heater also results in an increase in leakage current.

SUMMARY OF THE INVENTION

It is therefore a principal object of the present invention to avoid the disadvantages of the prior art.

It is another object of the present invention to provide a gas concentration measuring apparatus designed to correct an error contained in an output of a gas concentration sensor arising from control of supply of power to a heater built in the gas concentration sensor.

According to one aspect of the invention, there is provided a gas concentration measuring apparatus which comprises: (a) a gas concentration sensor including a sensor element producing a signal indicative of the concentration of a preselected component contained in gasses, a heater heating the sensor element, and an insulator disposed between the sensor element and the heater; (b) a heater control circuit controlling a supply of power to the heater of the gas concentration sensor; and (c) an error correcting circuit correcting an error contained in the signal produced by the sensor element of the gas concentration sensor arising from a leakage current flowing into the sensor element through the insulator during control of the supply of power to the heater by the heater control circuit.

In the preferred mode of the invention, the heater control circuit determines a target voltage to be applied to the heater for keeping a temperature of the sensor element of the gas concentration sensor at a given value required for activation of the sensor element and controls the supply of power to the heater based on the target voltage.

The heater control circuit limits a change in voltage applied to the heater when the gas concentration sensor is in a activated state to below a given value.

The heater control circuit includes, a power supply, a switching element, a coil, and a capacitor. The switching element is turned on and off to apply a voltage of the power supply to the heater cyclically. The coil and the capacitor serve to smooth the voltage of the power supply.

The switching frequency of the switching element is 1 kHz or more.

A filter may be provided which cuts off low frequency components below 100 Hz from the signal produced by the sensor element of the gas concentration sensor.

The may cut off low frequency components below at least the switching frequency from the signal produced by the sensor element of the gas concentration sensor.

The sensor element may include a first cell which is responsive to application of voltage to discharge oxygen contained in the gasses and produces a current signal as a function of a concentration of the oxygen and a second cell which is responsive to application of voltage to produce a current signal as a function of a concentration of a given gas component contained in the gasses after the oxygen is discharged through the first cell.

The sensor element may alternatively has a cell which produces an electromotive force as the gas concentration signal.

According to the second aspect of the invention, there is provided a gas concentration measuring apparatus which comprises: (a) a gas concentration sensor including a sensor element producing a signal indicative of the concentration of a preselected component contained in gasses, a heater heating the sensor element, and an insulator disposed between the sensor element and the heater; (b) a heater control circuit supplying power to the heater cyclically using a pulse-width modulated (PWM) signal; and (c) a filter passing frequency components of the signal produced by the sensor element within a given low frequency band. The frequency of the PWM signal is so determined as to allow the filter to compensate for an error which is contained in the signal inputted to the filter and which arises from the PWM signal.

In the preferred mode of the invention, the frequency of the PWM signal is ten or more times a cutoff frequency of the filter.

The PWM signal may be at least greater than a frequency of a change in signal outputted from the gas concentration sensor.

The cutoff frequency of the filter is less than or equal to 100 Hz.

The cutoff frequency of the filter may also be at least less than or equal to the frequency of the PWM signal.

A detecting circuit is provided which detects at least one of a voltage applied to the heater and a current flowing through the heater and a sample-and-hold circuit connected to an output of the detecting circuit.

The sensor element includes a first cell which is responsive to application of voltage to discharge oxygen contained in the gasses and produces a current signal as a function of a concentration of the oxygen and a second cell which is responsive to application of voltage to produce a current signal as a function of a concentration of a given gas component contained in the gasses after the oxygen is discharged through the first cell.

The sensor element may alternatively have a cell which produces an electromotive force as the gas concentration signal.

According to the third aspect of the invention, there is provided a gas concentration measuring apparatus which comprises: (a) a gas concentration sensor including a sensor element producing a signal indicative of the concentration of a preselected component contained in gasses, a heater heating the sensor element, and an insulator disposed between the sensor element and the heater, the heater being connected at a first end to a power supply and at a second end to ground; (b) a heater control circuit controlling a supply of power from the power supply to the heater of the gas concentration sensor; and (c) a switch disposed between the first end of the heater and the power supply, the switch establishing communication between the heater and the power supply when the power is supplied to the heater through the heater control circuit while blocking the communication when the supply of power to the heater is cut.

In the preferred mode of the invention, a second switch may also be disposed between the second end of the heater and the ground. The second switch establishes communication between the heater and the ground when the power is supplied to the heater through the heater control circuit while blocking the communication when the supply of power to the heater is cut.

According to the fourth aspect of the invention, there is provided a gas measuring apparatus which comprises: (a) a gas concentration sensor including a sensor element producing a gas concentration signal as a function of concentration of a specified component of gasses to be measured, a heater heating the sensor element, and an insulator disposed between the sensor element and the heater; (b) a heater control circuit controlling a supply of power to the heater of the gas concentration sensor in pulse-width modulation; and (c) a circuit detecting the gas concentration signal either for a power supply-on duration in which the power is supplied to the heater through the heater control circuit or for a power supply-off duration in which the supply of power to the heater is cut.

According to the fifth aspect of the invention, there is provided a gas concentration measuring apparatus which comprises: (a) a gas concentration sensor including a sensor element producing a gas concentration signal indicative of the concentration of a preselected component contained in gasses, a heater heating the sensor element, and an insulator disposed between the sensor element and the heater; (b) a heater control circuit supplying power to the heater cyclically using a pulse-width modulated (PWM) signal; and (c) a correction circuit monitoring values of the gas concentration signal in a power supply-on duration for which the power is supplied to the heater and a power supply-off duration for which supply of the power to the heater is cut off, the correction circuit corrects the gas concentration signal using the monitored values.

In the preferred mode of the invention, the correction circuit averages the values of the gas concentration signal in the power supply-on duration and the power supply-off duration and corrects the gas concentration signal using an averaged value.

The sensor element includes a first cell which is responsive to application of voltage to discharge oxygen contained in the gasses and produces a current signal as a function of a concentration of the oxygen and a second cell which is responsive to application of voltage to produce a current signal as a function of a concentration of a given gas component contained in the gasses after the oxygen is discharged through the first cell.

The sensor element may alternatively have a cell which produces an electromotive force as the gas concentration signal.

According to the sixth aspect of the invention, there is provided a gas concentration measuring apparatus which comprises: (a) a gas concentration sensor including a sensor element producing a gas concentration signal indicative of the concentration of a preselected component contained in gasses, a heater heating the sensor element, and an insulator disposed between the sensor element and the heater; (b) a heater control circuit supplying power to the heater cyclically using a pulse-width modulated (PWM) signal; and (c) a correction circuit estimating an error which is to be contained in the gas concentration signal and which arises from a leakage current flowing into the sensor element through the insulator caused by a change in resistance of the insulator produced during control of supply of the power to the heater by the heater control circuit using the PWM signal, the correction circuit removing the estimated error from the gas concentration signal.

In the preferred mode of the invention, the correction circuit corrects the gas concentration signal using a greater correction value as a voltage of a power supply for the heater increases.

The correction circuit corrects the gas concentration signal using a greater correction value as a temperature of the sensor element increases.

The sensor element includes a first cell which is responsive to application of voltage to discharge oxygen contained in the gasses and produces a current signal as a function of a concentration of the oxygen and a second cell which is responsive to application of voltage to produce a current signal as a function of a concentration of a given gas component contained in the gasses after the oxygen is discharged through the first cell.

The sensor element may alternatively have a cell which produces an electromotive force as the gas concentration signal.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 12(a) shows a change in NOx concentration;

FIG. 12(b) shows a change in output of a NOx concentration determining circuit;

FIG. 12(c) shows the waveform of an output of a NOx concentration determining circuit after passing through a low-pass filter;

FIG. 13(a) shows a duration for which the power is supplied to a heater if a PWM frequency is 1 kHz and the duty cycle of a PWM signal is 5%;

FIG. 13(b) shows a duration for which the supply of power to a heater is cut off if a PWM frequency is 1 kHz and the duty cycle of a PWM signal is 95%;

FIG. 16(a) shows a heater control signal;

FIG. 16(b) shows a NOx concentration signal;

FIG. 16(c) shows an error-corrected NOx concentration signal;

DESCRIPTION OF THE PREFERRED EMBODIMENTS

Figure 1:
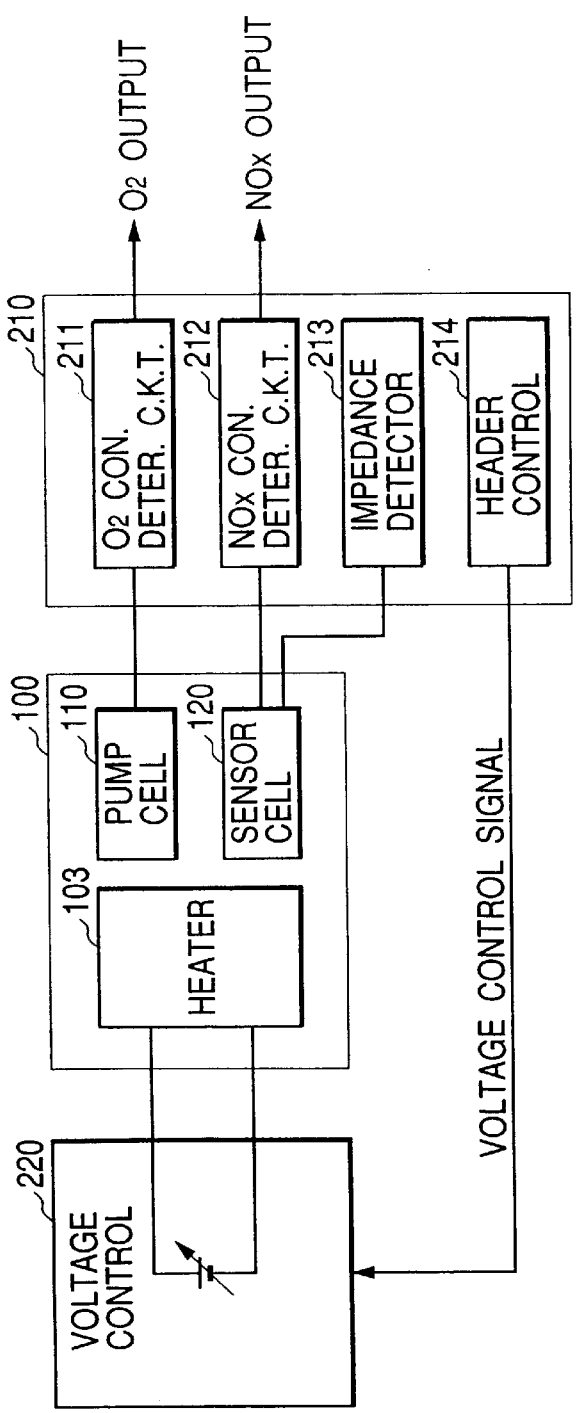
FIG. 1 is a block diagram which shows a gas concentration measuring apparatus according to the first embodiment of the invention.

Referring now to the drawings, wherein like numbers refer to like parts in several views, particularly to FIG. 1, there is shown a gas concentration measuring apparatus according to the first embodiment of the invention which is used with, as one example, an automotive control system designed to control the quantity of fuel injected into an internal combustion gasoline engine as a function of an output of the gas concentration measuring apparatus under feedback (F/B) control to bring the air-fuel (A/F) ratio into agreement with a target value. The gas concentration measuring apparatus uses a composite gas sensor capable of measuring concentrations of an oxygen ($O_2$) and nitrogen oxide (NOx) contained in exhaust gasses of the internal combustion engine simultaneously.

The output of the gas concentration measuring apparatus is also used in the control system to control a NOx catalytic converter (e.g., a NOx adsorption reduction catalytic converter) mounted in an exhaust pipe of the engine. Specifically, the control system determines the amount of NOx discharged from the NOx catalytic converter without being reacted or purified using an output of the gas concentration measuring apparatus and recovers the ability of NOx catalytic converter if the discharged amount of NOx is increased. Such recovery is achieved by supplying an enriched mixture to the NOx catalytic converter temporarily to remove ions adsorbed in the NOx catalytic converter.

The gas concentration measuring apparatus, as shown in FIG. 1, generally includes a gas concentration sensor 100, a sensor control circuit 210, and a voltage control circuit 220.

The gas concentration sensor 100 is installed in, for example, an exhaust pipe of the engine and includes a pump cell 110 for measuring the concentration of $O_2$, a sensor cell 120 for measuring the concentration of NOx, and a heater 103 connected to a typical storage battery mounted in the vehicle to produce heat for keeping the sensor 100 activated.

Figure 2:
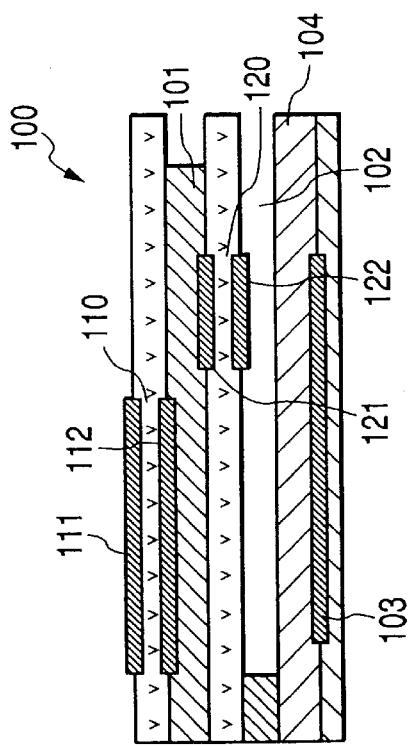
FIG. 2 is a sectional view which shows an internal structure of a gas concentration sensor.

The gas concentration sensor 100 has, as shown in FIG. 2, a two-cell structure designed to measure concentrations of $O_2$ and NOx contained in exhaust gasses of the internal combustion engine simultaneously. The gas concentration sensor 100 is made of a lamination of the pump cell 110, the sensor cell 120, a porous diffused layer 101, an air duct 102, an insulating layer 104, and the heater 103. The gas concentration sensor 100 is installed at the right side thereof, as viewed in the drawing, on an exhaust pipe of the engine so as to expose upper, lower, and left surfaces to exhaust gasses.

The pump cell 110 is disposed on the porous diffused layer 101 so that it is exposed to the exhaust gasses. A first pump electrode 111 is mounted on the upper surface of the pump cell 110. A second pump electrode 112 is mounted on the lower surface thereof facing the porous diffused layer 101. The sensor cell 120 is interposed between the porous diffused layer 101 and the air duct 102. A first sensor cell electrode 121 is attached to an upper surface of the sensor cell 120 facing the porous diffused layer 101. A second sensor cell electrode 122 is attached to a lower surface of the sensor cell 120 facing the air duct 102. The exhaust gasses enters the porous diffused layer 101 from the left side thereof, as viewed in the drawing, and flow in the right direction.

The pump cell 110 and the sensor cell 120 are each formed with a solid electrolyte lamination such as an oxygen ion conductive oxide sintered member made from $ZrO_2$, $HfO_2$, $ThO_2$, and $Bi_2O_3$ in which CaO, MgO, $Y_2O_3$, and $Yb_2O_3$ are solved as fixing agents. The porous diffused layer 101 is made of a heat-resisting inorganic matter such as alumina, magnesia, silica, spinel, and mullite.

The first pump cell electrode 111 and the first and second sensor cell electrodes 121 and 122 are each made of a noble metal with a high catalytic activity such as platinum, while the second pump electrode 112 is made of a noble metal such as Au-Pt which is inactive with respect to NOx, that is, hardly decomposes NOx.

The heater 103 is embedded in the insulating layer 104. The insulating layer 104 defines the air duct 102 between itself and the sensor cell 120. The air duct 102 serves as a reference gas chamber into which the air is introduced. The air in the reference gas chamber is used as a reference gas in measuring the concentration of $O_2$ The insulating layer 104 is made of alumina. The heater 103 is made of platinum and cermet such as alumina and supplied with power from the sensor control circuit 210 to produce the heat for activating the whole of the gas concentration sensor 100.

Figure 3A:
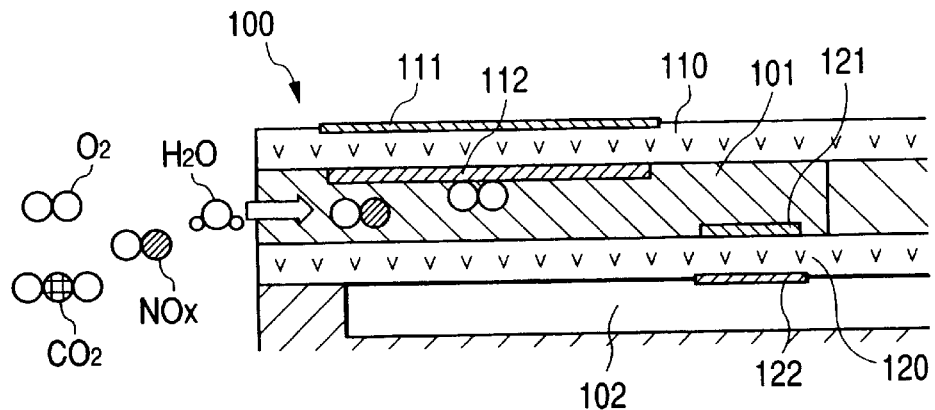
FIGS. 3(a), 3(b), and 3(c) are sectional views which show a sequence of gas measurement operations of a gas concentration sensor.
Figure 3B:
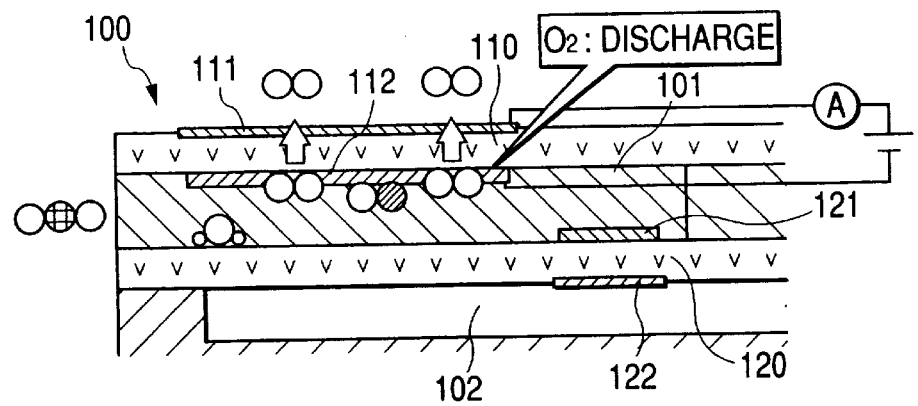
Figure 3C:
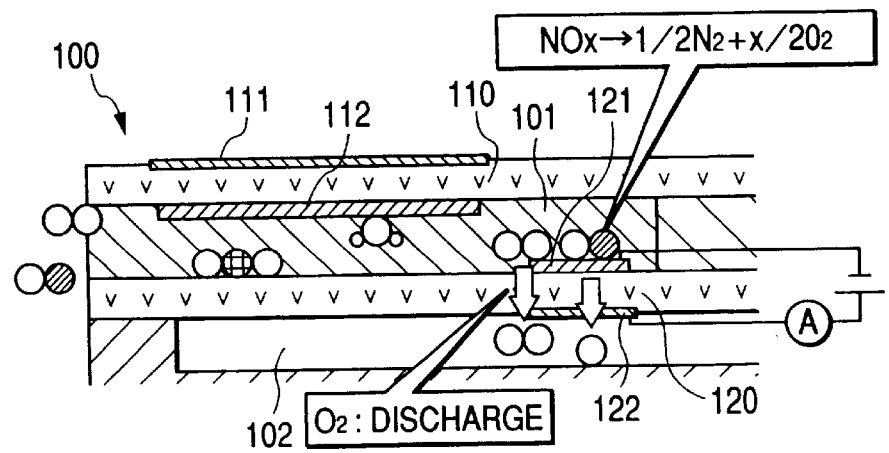

In operation, when exhaust gasses containing $O_2$, NOx, $CO_2$, and $H_2O$ enter, as shown in FIG. 3($a$), the porous diffused layer 101 and are passing the pump cell 110, application of voltage to the pump cell 110 through the electrodes 111 and 112 causes the exhaust gasses to undergo decomposition. Since the second pump cell electrode 112 is, as described above, made of a noble metal which hardly decomposes NOx, only $O_2$ molecules contained in the exhaust gasses are decomposed or ionized by the pump cell 100, as shown in FIG. 3($b$), which are, in turn, returned to the exhaust gasses from the first pump cell electrode 111, thereby causing a limiting current (also referred to as a pump cell current or $O_2$ current below) to flow through the pump cell 110 as a function of the concentration of $O_2$ in the exhaust gasses, which is, in turn, picked up by the sensor control circuit 210.

The $O_2$ molecules in the exhaust gasses are usually not decomposed by the pump cell 110 completely, so that residual O[<i]nf2 molecules reach the sensor cell 120. The application of voltage to the sensor cell 120 causes the first sensor cell electrode 121 to decompose the $O_2$ and NOx molecules, as shown in FIG. 3($c$), so that oxygen ions are discharged to the air duct 102 through the second sensor cell electrode 122, thereby causing a limiting current (also referred to as a sensor cell current or a NOx current below) to flow through the sensor cell 120 as a function of the concentration of NOx, which is, in turn, picked up by the sensor control circuit 210.

Figure 4:
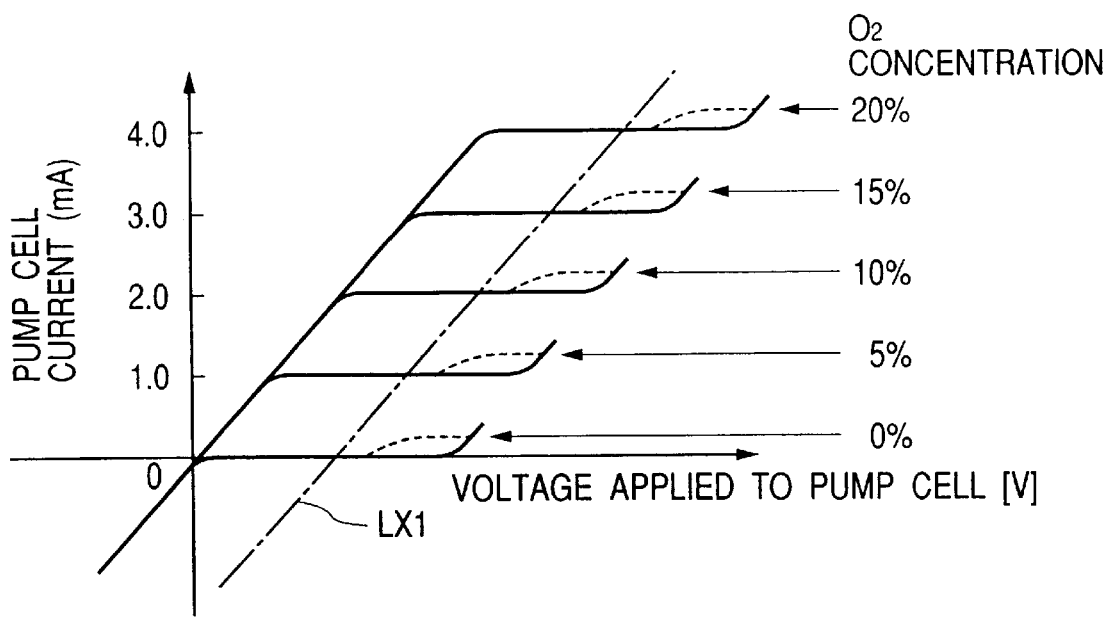
FIG. 4 is a graph which shows a relation between a pump cell current produced by a pump cell and a voltage applied to the pump cell.

FIG. 4 shows a V-I relation between the voltage applied to the pump cell 110 and the pump cell current (mA) outputted from the pump cell 110. Straight segments of lines extending parallel to the abscissa axis indicate limiting current measurable ranges, respectively, which are shifted to the positive side of voltage applied to the pump cell 110 as the concentration of $O_2$ increases. The second pump cell electrode 112 of the pump cell 110 is, as described above, made of material which hardly decomposes NOx, so that NOx molecules in the exhaust gasses are hardly decomposed, but if the voltage applied to the pump cell 110 exceeds a certain upper limit in each limiting current measurable range, it will cause the NOx molecules to be decomposed, thereby producing the pump cell current, as indicated by a broken line, containing components depending upon the concentration of NOx as well as the concentration of $O_2$.

Figure 5:
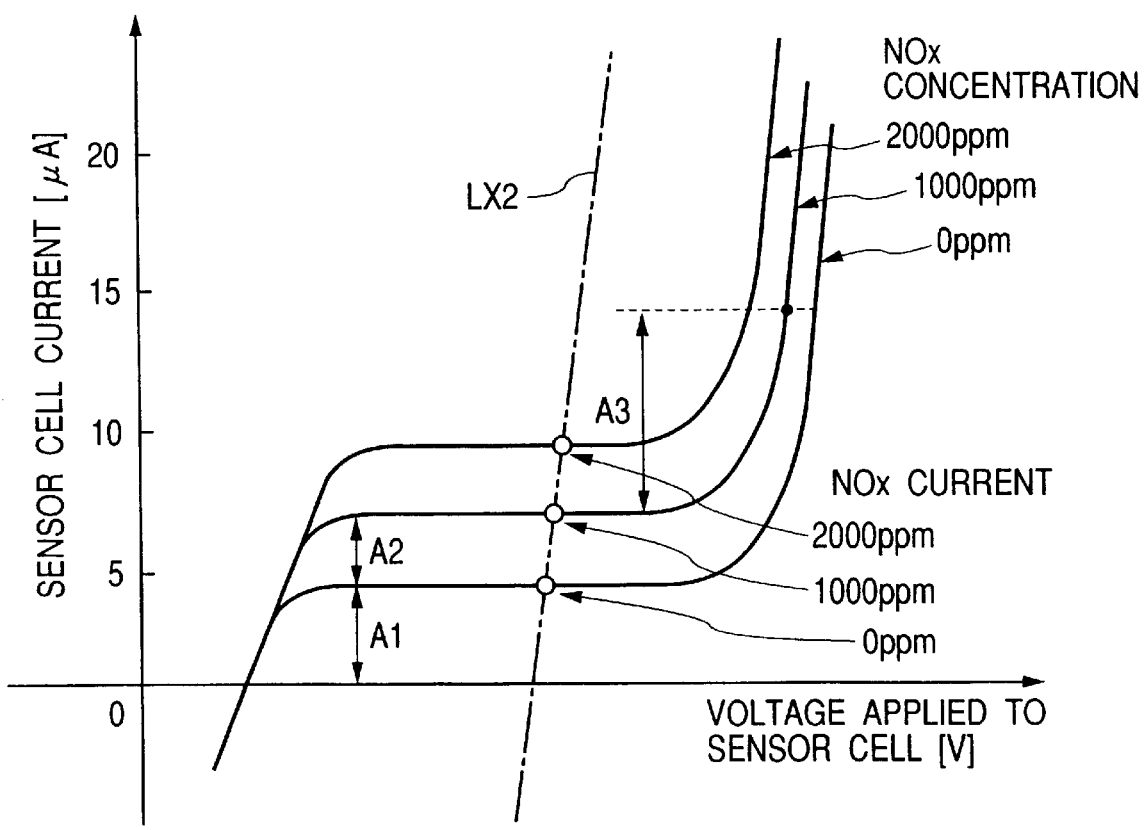
FIG. 5 is a graph which shows a relation between a sensor cell current flowing through a sensor cell and a voltage applied to the sensor cell.

FIG. 5 shows a V-I relation between the voltage applied to the sensor cell 120 and the sensor cell current (mA) outputted from the sensor cell 120. In a range where the concentration of NOx is zero (0) ppm, only a current, as indicated by A1, produced by the residual $O_2$ molecules flowing through the porous diffused layer 101 to the sensor cell 120 is outputted from the sensor cell 120 as the offset current. In a range where the concentration of NOx is greater than zero (0) and smaller than 1,000 ppm, a current, as indicated by A2, produced by the decomposition of NOx by the sensor cell 120 is also outputted from the sensor cell 120. If the voltage applied to the sensor cell 120 exceeds a certain upper limit, it will cause an additional current, as indicated by A3, produced by decomposition of $H_2O$ to be also outputted from the sensor cell 120. Straight segments of lines extending parallel to the abscissa axis indicate limiting current measurable ranges, respectively, where it is possible to measure the NOx decomposition-produced current and which are slightly shifted to the positive side of voltage applied to the sensor cell 120 as the concentration of NOx increases.

The sensor control circuit 210, as shown in FIG. 1, includes an oxygen concentration determining circuit 211, a NOx concentration determining circuit 212, an impedance measuring circuit 213, and a heater control circuit 214.

The oxygen concentration determining circuit 211 is connected to the pump cell 110 of the gas concentration sensor 100 to apply the voltage thereto and measure an electric current flowing through the pump cell 110 as a function of the concentration of $O_2$ and outputs a sensor signal indicative of the concentration of $O_2$. The NOx concentration determining circuit 212 is connected to the sensor cell 120 to apply the voltage thereto and measure an electric current flowing through the sensor cell 120 as a function of the concentration of NOx and outputs a sensor signal indicative of the concentration of NOx.

The impedance measuring circuit 213 determines the impedance of the sensor cell 120 (also referred to as a sensor element impedance below) using, for example, a sweep method for determining the temperature of the gas concentration sensor 100. Specifically, the determination of the sensor element impedance is achieved by changing the voltage applied to the sensor cell 120 by a given level instantaneously, detects a change in sensor cell current caused thereby, and looking up a table listing a relation between the voltage applied to the sensor cell 120 and a change in sensor cell current. The determination of the sensor element impedance is made, for example, at intervals of 128 ms just after start-up of the engine and at intervals of 256 ms after the engine warms up.

Figure 7:
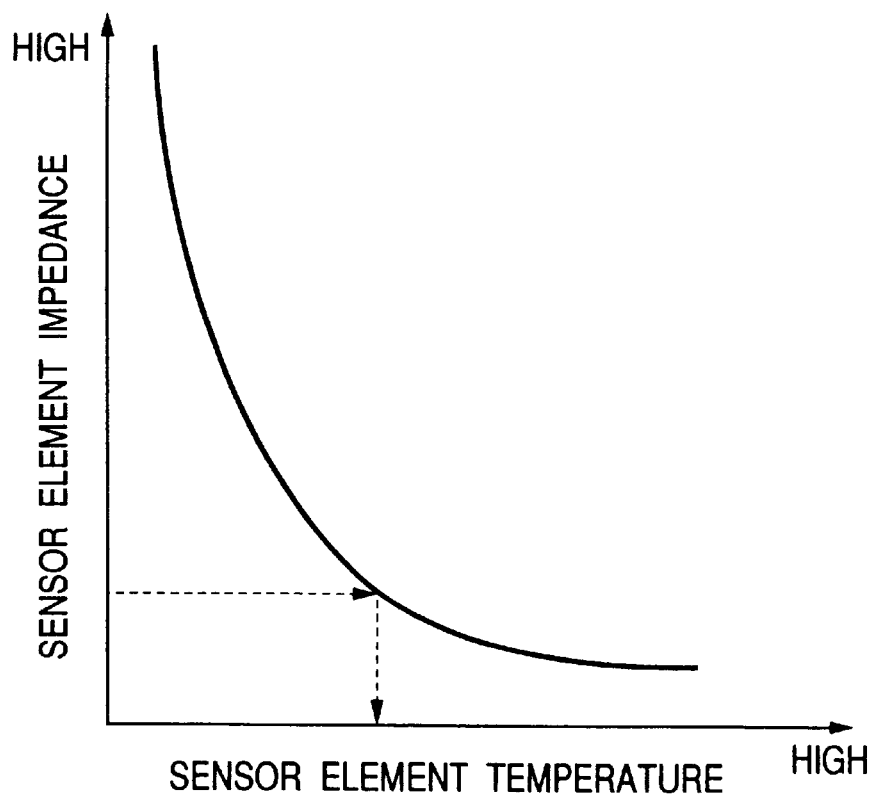
FIG. 7 is a graph which shows a relation between the impedance of a sensor element of a gas concentration sensor and the temperature of the sensor element.

The heater control circuit 214 converts the sensor element impedance measured by the impedance measuring circuit 213 into the temperature of the sensor cell 120 (also referred to as a sensor element temperature below). The sensor element impedance has a relation to the sensor element temperature, as shown in FIG. 7, in which the sensor element impedance increases greatly as the sensor element temperature decreases. The heater control circuit 214 determines a voltage control signal for bringing the sensor element temperature into agreement with a target value under feedback control and outputs it to the voltage control circuit 220.

Figure 6:
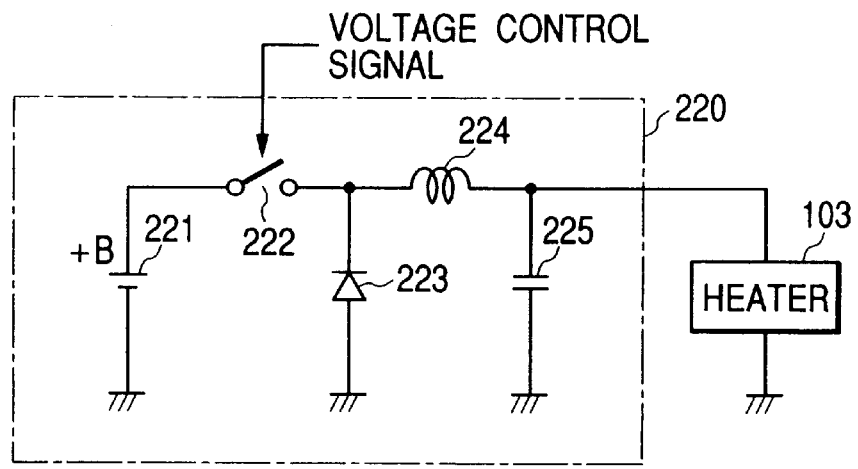
FIG. 6 is an illustration which shows a circuit structure of a voltage control circuit for a heater.

The voltage control circuit 220 is responsive to the voltage control signal from the heater control circuit 214 to control a supply of power to the heater 103. The voltage control circuit 220 may be made of a switching power supply circuit, as shown in FIG. 6, which is designed to provide a dc voltage to the heater 103 to control the heat generated thereby. The switching power supply circuit includes a power supply 221, a switching transistor 222, a diode 223, a coil 224, and a capacitor 225. The switching transistor 222 is responsive to input of the voltage control signal to be turned on and off at high speeds to control an output voltage of the voltage control circuit 220 applied to the heater 103. The coil 224 and the capacitor 225 serve to smooth the source voltage +B during the on-off operation of the switching transistor 222. The diode 223 has the coil 224 discharge energy stored therein when the switching transistor 222 is turned off. The switching transistor 222 is turned on and off at several tens kHz for decreasing the size of the voltage control circuit 220, improving the efficiency of power supply, and minimizing a variation of voltage applied to the heater 103.

As one example, if the resistance of the heater 103 when the gas concentration sensor 100 is in an activated state is approximately 4.5 Ω, the switching frequency to turn on and off the switching transistor 222 is set to 16 kHz, the capacitance of the capacitor 225 is set to 820 μF, and the inductance of the coil 224 is set to 36 μH. This allows a variation in voltage applied to the heater 103 when the gas concentration sensor 100 is in the activated state to be kept below a given level (e.g., 2V). For instance, if the source voltage +B applied to the heater 103 is 14V, 7V appears at the middle between the terminals of the heater 103. If the resistance of the insulating layer 104 during the on-off control of supply of power to the heater is 6M Q a leakage current of 1.2 μA (=7V/6MΩ) flows to the sensor cell 120 through the insulating layer 104. If an output current of the gas concentration sensor 100 when the NOx concentration is 1000 ppm is 4 μA, an error equivalent to 30% (=1.2 μA/4 μA) of the output current of the gas concentration sensor 100 is produced in a dynamic range of 1000 pm, so that a sensor output will contain an error corresponding to approximately 300 ppm arising from the leakage current. Therefore, decreasing the error in an output of the gas concentration sensor 100 below 5% requires keeping the variation in voltage applied to the heater 103 when the gas concentration sensor 100 is activated below approximately 2V. This accuracy of the sensor output may be maintained by determining the capacitance of the capacitor 225 and the inductance of the coil 224 depending upon the resistance of the heater 103. However, the degree of influence of the leakage current on the sensor output will be changed by various factors such as a positional relation between the sensor element and the heater 103 and the sensor structure (e.g., material and size). It is, thus, advisable that the variation in voltage applied to the heater 103 be determined taking the above factors into consideration.

Low-pass filters (not shown) may be connected to outputs of the $O_2$ concentration determining circuit 211 and the NOx concentration determining circuit 212 of the sensor control circuit 210, respectively. The cutoff frequency of the low-pass filters is set to at least the switching frequency of the voltage control circuit 220, thereby minimizing undesirable effects of a change in the voltage of the heater 103, improving the accuracy of the sensor output. For instance, if the frequency of a change in sensor output is on the order of 10 Hz, the cutoff frequency is preferably 100 Hz or less. The use of the low-pass filters allows variations in output from the $O_2$ concentration determining circuit 211 and the NOx concentration determining circuit 212 at relatively high frequencies to be decreased, thereby assuring a higher accuracy of outputs of the gas concentration sensor 100.

Figure 8A:
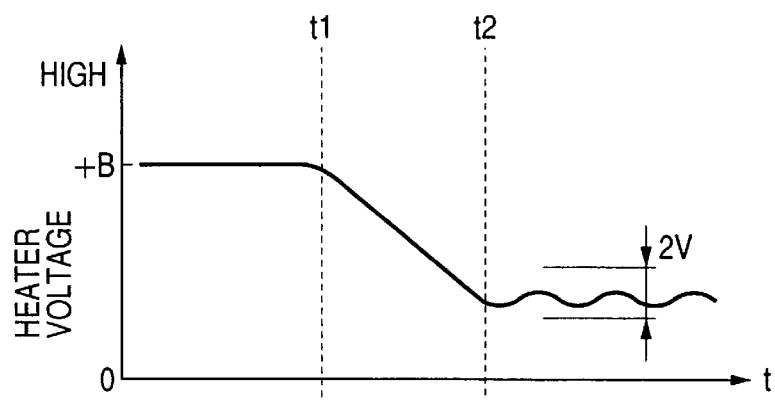
FIG. 8(a) shows a change in voltage applied to a heater.
Figure 8B:
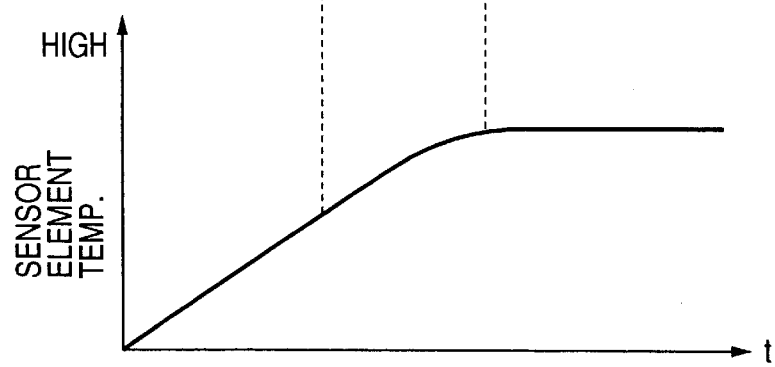
FIG. 8(b) shows a change in temperature of a sensor element.

FIGS. 8(*a*) and 8(*b*) are time charts indicating changes in voltage of the heater 103 (i.e., voltage appearing across terminals of the heater 103) and temperature of the sensor element, respectively, just after start-up of the engine. When the engine is still in a cold condition after the start-up of the engine, the source voltage +B, as shown in FIG. 6, is applied directly to the heater 103 for speeding up the activation of the gas concentration sensor 100. Specifically, the switching transistor 222 is kept turned on.

Upon initiation of the activation of the gas concentration sensor 100 after t1, the voltage control signal inputted to the voltage control circuit 220 is so controlled as to decrease the voltage applied to the heater 103 gradually. This causes the voltage applied to the heater 103 during an interval between t1 and t2 until the gas concentration sensor 100 becomes activated completely to undergo a great change. However, the insulating resistance of the insulating layer 104 made of alumina is relatively high, thereby decreasing the influence of the leakage current on the sensor element of the gas concentration sensor 100 to avoid an undesirable change in sensor output indicative of the NOx concentration.

After the gas concentration sensor 100 is activated completely at t2, the insulating resistance of the insulating layer 104 decreases, so that a sensor output indicative of the NOx concentration will contain an error caused by the leakage current. However, a variation in voltage applied to the heater 103 is controlled by the voltage control signal to be kept below 2V, thereby minimizing the influence of the leakage current on the sensor output of the NOx concentration.

The above described first embodiment of the invention has the advantages as discussed below. (1) The voltage control signal to have the sensor element temperature of the gas concentration sensor 100 reach a target value under feedback control is, as described above, used in controlling the supply of power to the heater 103, thereby minimizing the variation in output of the gas concentration sensor 100 caused by the control of the heater 103 as compared with a prior art system in which the supply of power to a heater is controlled in on-off cycles of several Hz to several tens Hz.

Specifically, a variation in voltage applied to the heater 103 is kept small, thus minimizing the influence of the leakage current flowing to the sensor element (i.e., the sensor cell 120) through the insulating layer 104 on an output from the sensor element. Even if the source voltage +B (i.e., the output voltage of the battery mounted in the vehicle) of the voltage control circuit 220 changes, the control of the heater 103 may be achieved without being influenced by the change in source voltage +B, thereby assuring the accuracy of measurement of the NOx concentration during the control of the heater 103. (2) The NOx current produced by the sensor cell 120 is weak, so that it may contain an error caused by the leakage current flowing to the sensor cell 120 during the on-off control of the heater 103. However, the first embodiment minimizes such an error and assures a higher accuracy of measurement of the NOx concentration. (3) The variation in voltage applied to the heater 103 after the gas concentration sensor 100 is activated is limited to a smaller value (e.g., 2V or less), thereby decreasing the influence of the leakage current on the sensor output further. (4) The voltage control circuit 220 includes the switching transistor 222, the coil 224, and the capacitor 225, thereby decreasing the variation in voltage applied to the heater 103 to decrease the influence of the leakage current on the sensor output further. Moreover, as compared with when a typical constant-voltage circuit having a dropper power supply designed to control a difference between the voltage of the power supply and a controlled voltage using a resistor is used, the heat dissipated from the transistor 222 is small, thereby allowing the voltage control circuit 220 to be decreased in size and increasing the efficiency thereof. The diode 223 works as a switching power supply to discharge the energy stored in the coil 224 when the switching transistor 222 is turned off, thereby decreasing the variation in voltage applied to the heater 103 further. (5) The switching frequency of the voltage control circuit 220 is at least more than or equal to the frequency of a change in sensor output (i.e., the $O_2$ current or the NOx current), thereby allowing the sensor output to be separated into a wanted component and an unwanted component by filtering. The switching frequency also impinges upon the accuracy of the sensor output and thus is preferably determined so as to meet accuracy requirements. For instance, the switching frequency is more than or equal to 1 kHz, thereby alleviating problems of increases in size and production cost of the circuit and decreasing the influence of a ripple. This realizes the gas concentration measuring apparatus suitable for use in automotive vehicles. Specifically, too low the switching frequency increases a ripple of the switching power supply (i.e., the voltage control circuit 220) excessively. The elimination of this problem requires increase in capacity of the capacitor 221, thus resulting in increases in size and production cost of the voltage control circuit 220. The use of the switching frequency more than or equal to 1 kHz in the voltage control circuit 220 of the first embodiment eliminates the problem related to the ripple without any penalties.

The second embodiment of the gas concentration measuring apparatus will be discussed below.

In typical devices which control a supply of power to a heater in an on-off operation using a pulse-width modulated (PWM) signal, a PWM frequency lies within a range of several Hz to several tens Hz (e.g., 8 Hz), which matches up with the frequency of a sensor output indicative of the concentration of NOx. In the second embodiment, the PWM frequency used for control of the heater 103 is increased up to several hundreds Hz to several kHz (e.g., 1 kHz). In this case, the on-off control of supply of power to the heater 103 effected at a frequency of several hundreds Hz to several kHz adds an error component to the NOx current produced by the sensor cell 120. The second embodiment is designed to compensates for such an error component by removing high frequency components arising from the on-off control of the power supply to the heater 103 from the NOx current.

Figure 9:
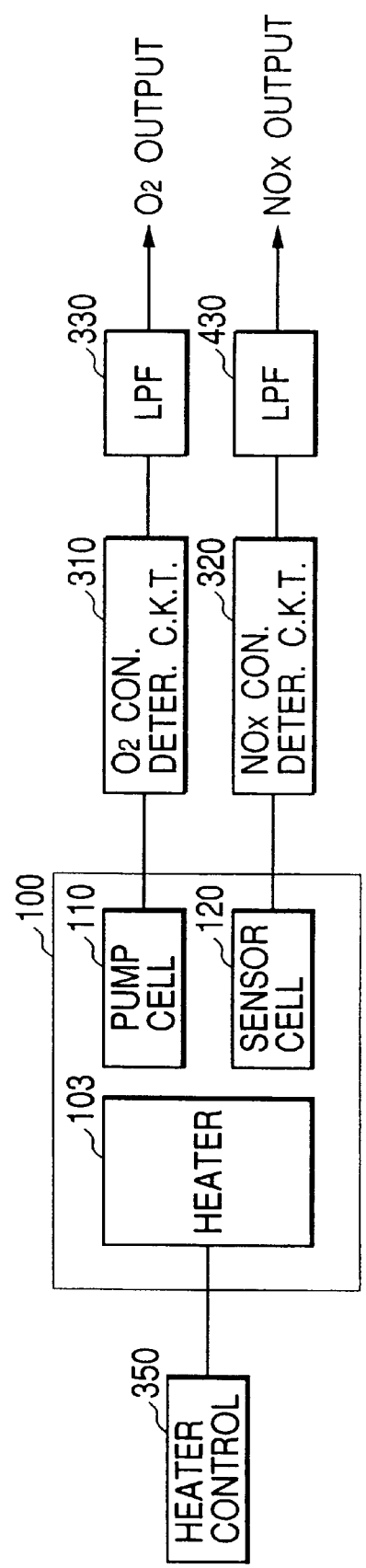
FIG. 9 is a block diagram which shows a gas concentration measuring apparatus according to the second embodiment of the invention.

FIG. 9 shows a circuit structure of the gas concentration sensor according to the second embodiment of the invention. The same reference numbers as employed in the first embodiment refer to the same parts, and explanation thereof in detail will be omitted here.

The heater 103 is PWM-controlled at a frequency of 1 kHz by the heater control circuit 350 consisting of a microcomputer. Like the first embodiment, the pump cell current flows through the pump cell 110 as a function of the concentration of $O_2$ contained in exhaust gasses of the engine and is measured by the $O_2$ concentration determining circuit 310, while the sensor cell current flows through the sensor cell 120 as a function of the concentration of NOx contained in the exhaust gasses and is measured by the NOx concentration determining circuit 320. The $O_2$ concentration determining circuit 310 and the NOx concentration determining circuit 320 convert the pump cell current and the sensor cell current into voltage signals and output them.

The low-pass filters 330 and 340 are connected to outputs of the $O_2$ concentration determining circuit 310 and the NOx concentration determining circuit 320. The low-pass filters 330 and 340 have a cutoff frequency of several tens Hz and cuts high frequencies containing a component produced by the on-off control of the power supply to the heater 103 out of outputs of the $O_2$ concentration determining circuit 310 and the NOx concentration determining circuit 320 to produce an A/F output (i.e., $O_2$ concentration output) and a NOx concentration output.

Figure 10:
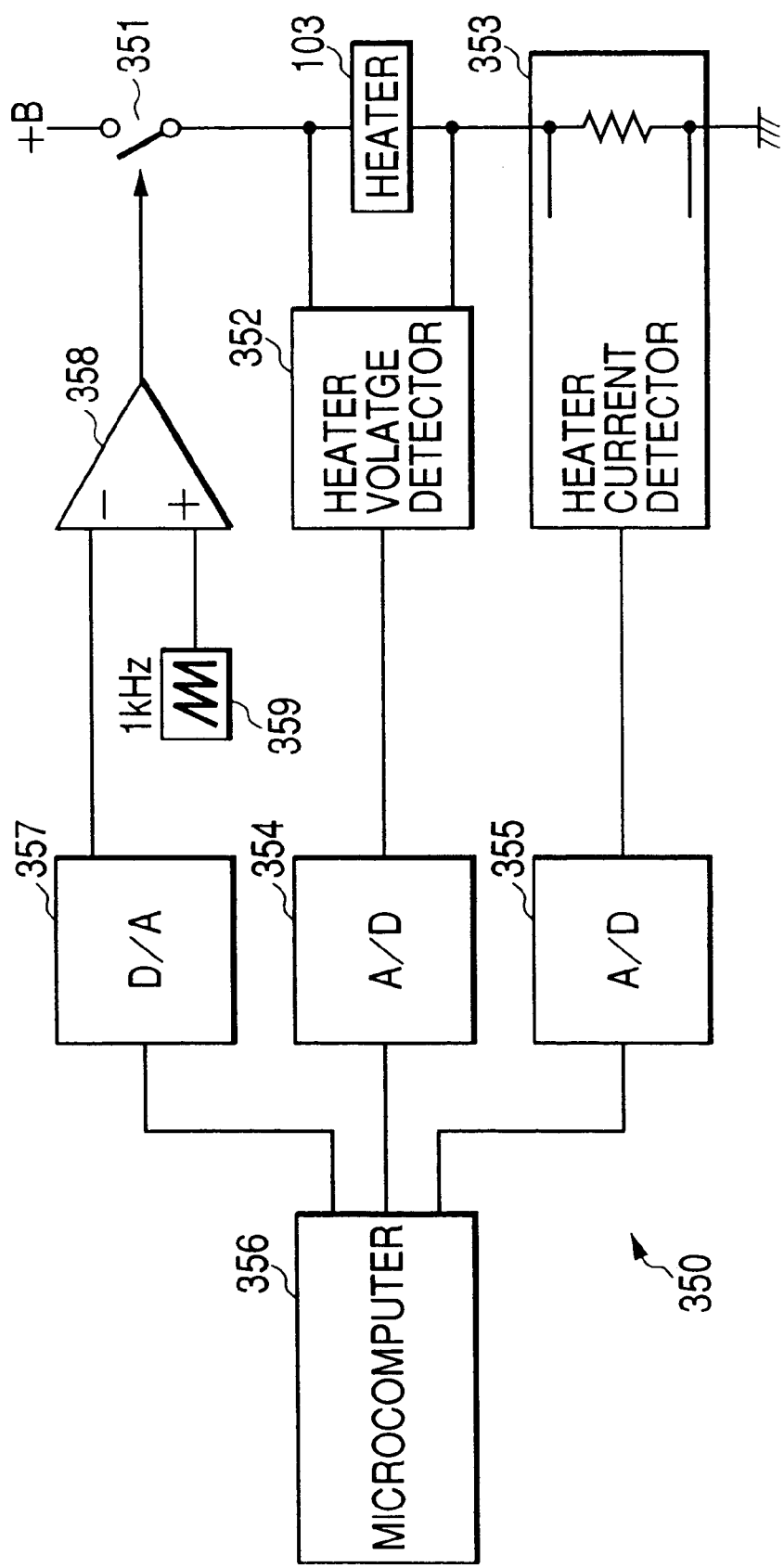
FIG. 10 is a block diagram which shows a structure of a heater control circuit.

The heater control circuit 350 is, as shown in FIG. 10, of a high side switch type and includes a switch 352, a heater voltage detector 352, a heater current detector 353, a D/A converter 357, A/D converters 354 and 355, a microcomputer 356, a comparator 358, and an oscillator 359. The switch 351 is disposed between a battery +B mounted in the vehicle (i.e., a power supply) and the heater 103. The heater voltage detector 352 detects the terminal voltage of the heater 103. The heater current detector 353 detects the current flowing through the heater 103. The heater voltage detector 352 and the heater current detector 353 provides outputs to the microcomputer 356 through the A/D converters 354 and 355.

The microcomputer 356 modifies an output of the D/A converter 357 to produce an analog voltage variation and supplies the voltage signal to a non-inverting input of the comparator 358. The oscillator 359 produces a sawtooth wave at 1 kHz and outputs it to an inverting input of the comparator 358. The comparator 358 compares the inputs to produce a PWM wave signal and outputs it to the switch 351 as a heater control signal. The switch 351 is then turned on and off at a frequency of 1 kHz to control a supply of power to the heater 103.

Figure 11:
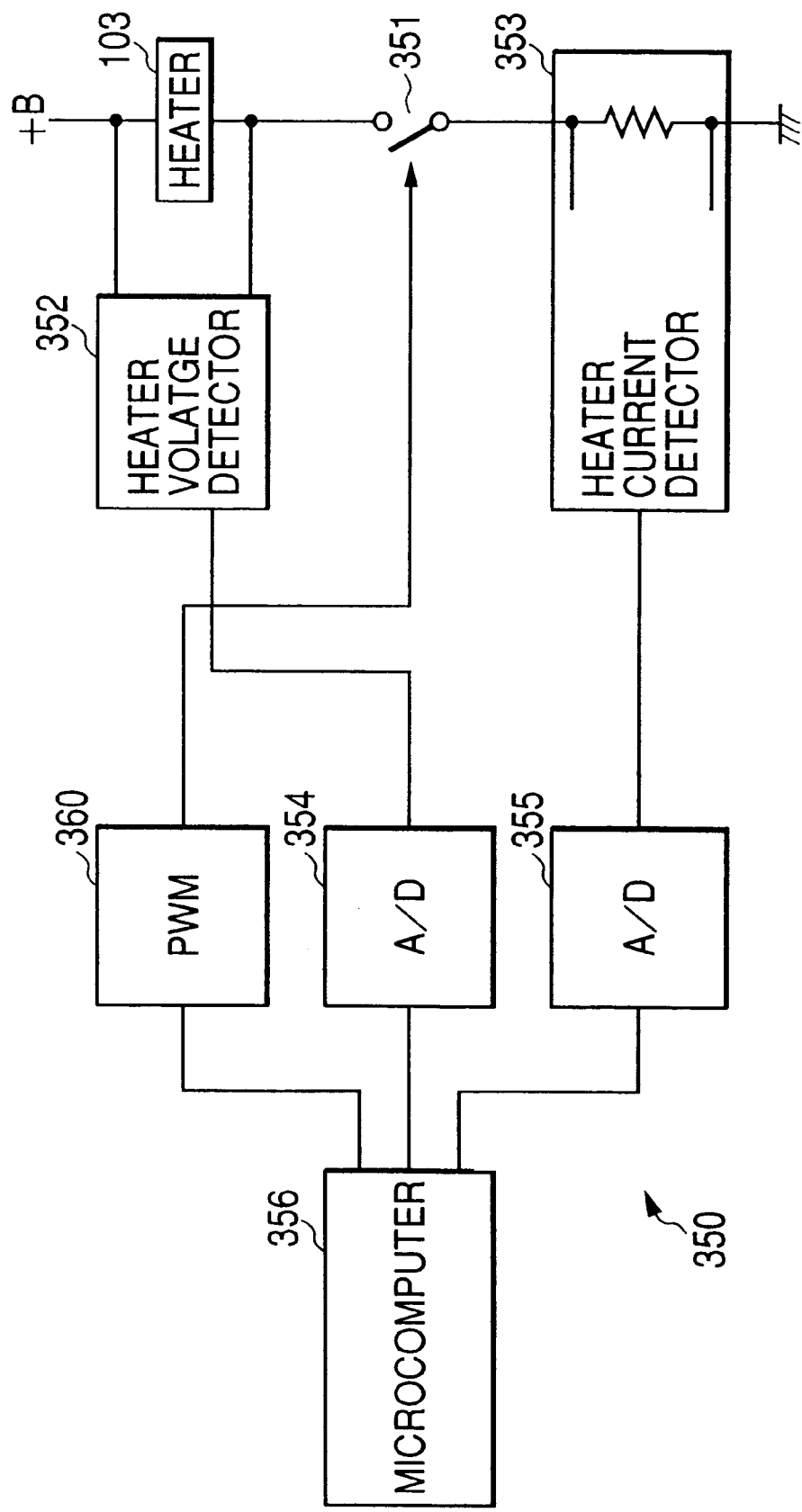
FIG. 11 is a block diagram which shows a modification of a heater control circuit.

The heater control circuit 350 may alternatively have a low side switch structure, as shown in FIG. 11. The same reference numbers as employed in FIG. 10 refer to the same parts, and explanation thereof in detail will be omitted here.

The switch 351 is disposed between the heater 103 and the heater current detector 353. The microcomputer 356 provides a control signal to a PWM circuit 360 made of an IC. The PWM circuit 360 controls an on-off operation of the switch 351 with a PWM frequency of, for example, 1 kHz.

In operation, when the concentration of NOx changes, as shown in FIG. 12(a), the NOx concentration determining circuit 320 produces an output, as shown in FIG. 12(b), containing an error component arising from the leakage current flowing into the sensor element of the gas concentration sensor 100 during the on-off control of the power supply to the heater 103. Specifically, the heater control signal is added to the output of the NOx concentration determining circuit 320. As described above, a signal indicative of the concentration of NOx (i.e., the NOx current) changes at several Hz to several tens Hz, and the on-off control of the power supply to the heater 103 is carried out at 1 kHz. The low-pass filter 340, therefore, cuts the heater control signal in the form of a high frequency wave out of the output of the NOx concentration determining circuit 320 to produce only a low frequency component, as shown in FIG. 12(c), indicating the concentration of NOx correctly.

The low-pass filter 330, like the low-pass filter 340, cuts the heater control signal (i.e., the error component arising from the leakage current flowing into the sensor element of the gas concentration sensor 100 during the on-off control of the power supply to the heater 103) out of the output of the $O_2$ concentration determining circuit 310 to produce only a low frequency component indicating the concentration of $O_2$ correctly. However, the NOx current is weaker than the $O_2$ current (i.e., the output of the $O_2$ concentration determining circuit 310), so that the NOx current is more influenced by the leakage current. Only the low-pass filter 340 may, thus, alternatively be provided.

The cutoff frequency of the low-pass filters 330 and 340 is, as described above, several tens Hz, while the PWM frequency is 1 kHz, however, these frequencies are not limited to the above values. It is advisable that the PWM frequency be set to at least more than or equal to the frequency of a change in sensor output. Additionally, the PWM frequency is preferably set to ten or more times the cutoff frequency of the low-pass filters 330 and 340. It is also advisable that the cutoff frequency of the low-pass filters 330 and 340 be at least less than or equal to the FWM frequency. For instance, the cutoff frequency is preferably less than or equal to 100 Hz because frequencies less than or equal to 100 Hz do not interfere with frequencies of signals used in air-fuel ratio control performed for every cylinder of the engine.

The third embodiment of the gas concentration measuring apparatus will be discussed below.

When the frequency of the PWM signal used in the on-off control of the power supply to the heater 103 is increased, as in the second embodiment, up to 1 kHz, it will cause a difficulty to be encountered in measuring the heater voltage and heater current. The heater voltage and heater current may be used in a failsafe operation to detect an accidental cutoff of the power supply to the heater 103 and in the on-off control of the power supply to the heater 103 to determine the quantity of power to be supplied to the heater 103.

For instance, in the structure, as shown in FIG. 10, if an on-duration in which the power is supplied to the heater 103 in the on-off control (also referred to as a power supply on-duration below) or an off-duration in which the supply of power to the heater 103 is cut (also referred to as a power supply off-duration) is too short, it will cause times required for the A/D converters 354 and 356 to convert an analog input into a digital output to the microcomputer 356 to become insufficient to determine the heater voltage and the heater current correctly. Specifically, if the PWM frequency is, as shown in FIG. 13(a), 1 kHz, and the duty cycle of the PWM signal is 5%, the power supply on-duration will be no more than 50 μsec. Alternatively, if the PWM frequency is, as shown in FIG. 13(b), 1 kHz, and the duty cycle of the PWM signal is 95%, the power supply off-duration will be no more than 50 μsec. In the cases shown in FIGS. 13(a) and 13(b), if an input voltage to each of the A/D converters 354 and 355 changes prior to completion of an A/D conversion, it becomes impossible to perform the A/D conversion correctly. High-speed A/D converters designed to perform a completion conversion within a conversion time of 35 μsec. are, thus, required to determine the heater voltage and the heater current precisely. The use of such high-speed A/D converters, however, leads to a difficulty in determining when the conversion should be started. Particularly, in a case where an IC is used for PWM, it is difficult to find the beginnings of the power supply on- and off-durations. In other words, it is difficult to start an appropriate A/D conversion, which may result in a failure in determining the heater voltage and the heater current. Additionally, a load of software is increased for controlling the start of the A/D conversion, thereby resulting in a difficulty in controlling the whole of the system and an increase in production cost of the system.

In order to avoid the above problems, the third embodiment of the invention is, as described later in detail, designed to retain heater voltages and heater currents measured both in the power supply on- and off-durations in sample-and-hold circuits temporarily.

Figure 14:
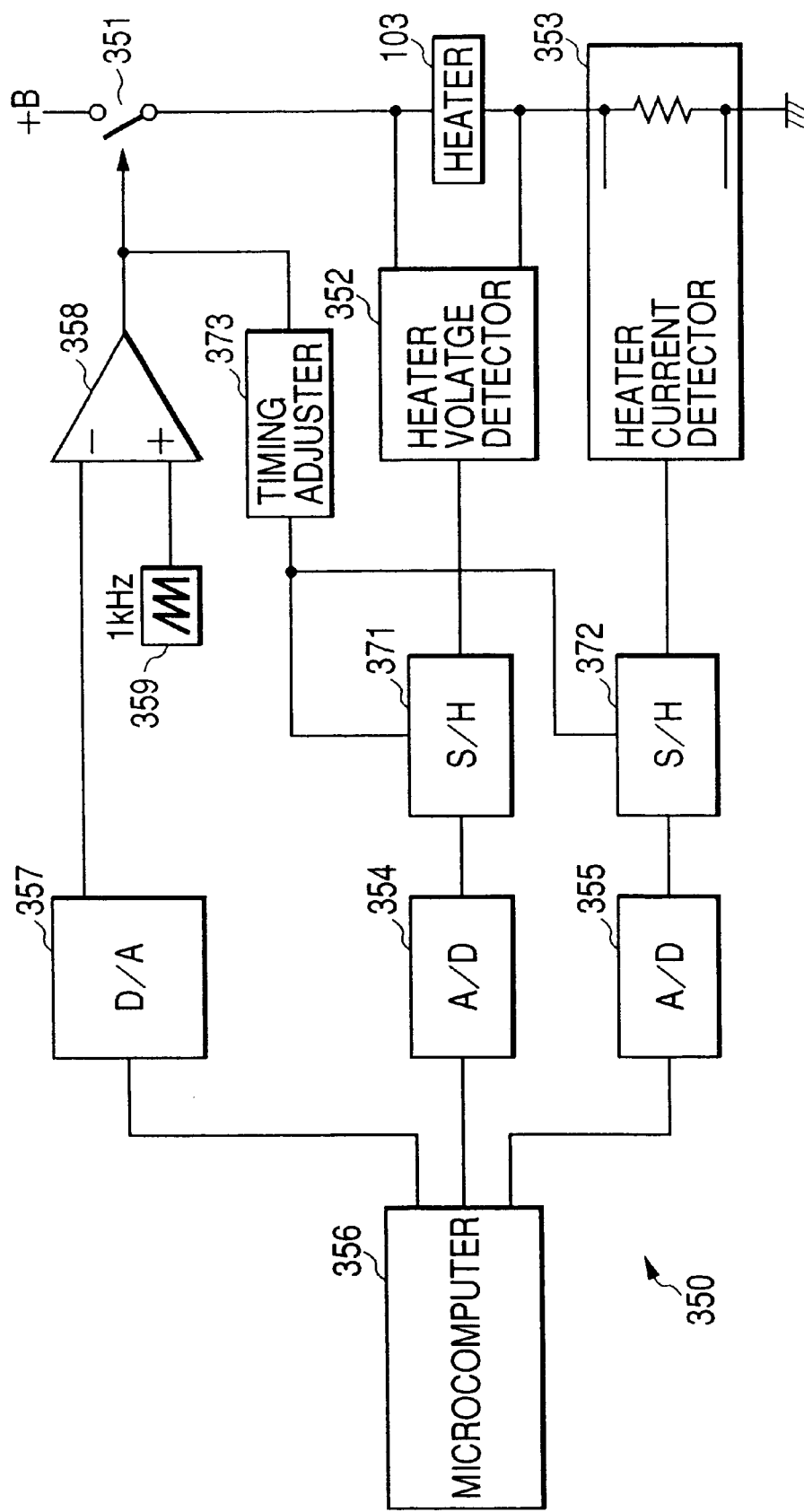
FIG. 14 is a circuit diagram which shows a heater control circuit according to the third embodiment of the invention.

FIG. 14 shows the heater control circuit 350 according to the third embodiment of the invention. The same reference numbers as employed in FIG. 10 refer to the same parts, and explanation thereof in detail will be omitted here.

The heater control circuit 350 includes sample-and-hold circuits 371 and 372 and a timing adjuster 373.

The timing adjuster 373 produces start signals in response to a change in the heater control signal to the switch 351. The sample-and-hold circuits 371 and 372 are connected to the heater voltage detector 352 and the heater current detector 353, respectively, and responsive to the start signals from the timing adjuster 373 to retain heater voltages and heater currents both in the power supply on- and off-durations. Even if the heater control signal inputted to the switch 351 changes, the values of the heater voltage and the heater current (i.e., outputs of the heater voltage detector 352 and the heater current detector 353) do not follow it instantaneously. The timing adjuster 373, thus, outputs the start signals a given period of time after the heater control signal is turned on and off to the sample-and-hold circuits 371 and 372 to hold the outputs of the heater voltage detector 352 and the heater current detector 353. Outputs of the sample-and-hold circuits 371 and 372 are inputted to the microcomputer 356 through the A/D converters 354 and 355. This allows the microcomputer 356 to determine the heater voltage and heater current correctly even during the PWM control of the power supply to the heater 103 at a high speed (1 kHz).

Track and hold type A/D converters designed to perform both a sample-and-hold operation and an A/D conversion may alternatively be used instead of the A/D converters 354 and 355 and the sample-and-hold circuits 371 and 372.

The fourth embodiment of the invention will be described below which is designed to average values of voltage outputs produced from the NOx currents indicating the concentration of NOx in the power supply on- and off-durations to minimize errors arising from the PWM signal both in the power supply on- and off-durations.

Figure 15:
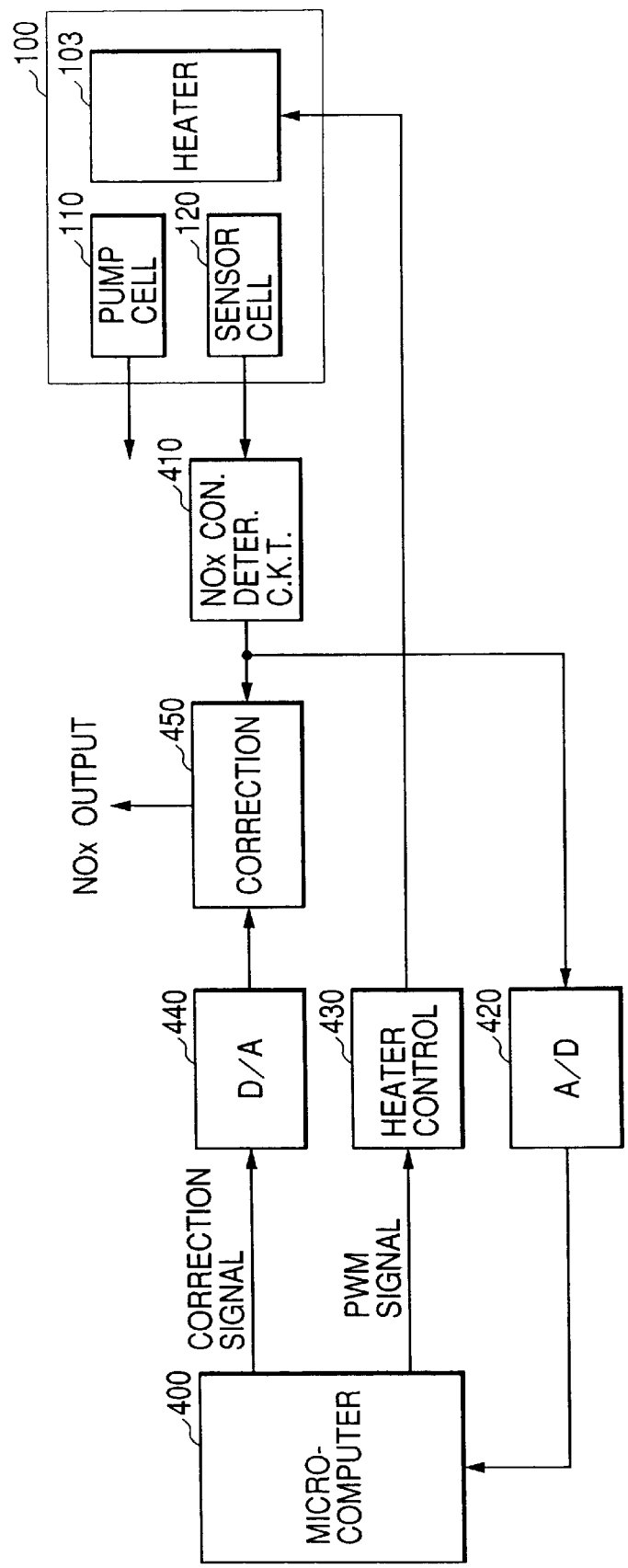
FIG. 15 is a block diagram which shows a gas concentration measuring apparatus according to the fourth embodiment of the invention.

FIG. 15 shows a gas concentration measuring apparatus according to the fourth embodiment of the invention.

The NOx concentration determining circuit 410 converts the NOx current flowing through the sensor cell 120 into a voltage signal indicating the concentration of NOx and outputs it to the correction circuit 450 and the microcomputer 400 through the A/D converter 420.

The microcomputer 400 provides a PWM signal of a several Hz to several tens Hz (e.g., 7.8 Hz) to the heater control circuit 430. The heater control circuit 430 performs, like the above embodiments, the on-off control of supply of power to the heater 103. The microcomputer 400 averages the outputs of the NOx concentration determining circuit 410 provided both in the power supply on- and off-durations to provide a correction signal to the correction circuit 450 through the D/A converter 440. The correction circuit 450 uses the correction signal to correct the NOx concentration signal inputted from the NOx concentration determining circuit 410 and produces an error-corrected NOx concentration signal.

FIGS. 16(a), 16(b), and 16(c) show variations in the heater control signal used in the on-off control of supply of power to the heater 103, the NOx concentration signal inputted to the microcomputer 400 from the NOx concentration determining circuit 410, and the eror-corrected NOx concentration signal outputted from the correction circuit 450, respectively.

As can be seen from the drawings, the NOx concentration signal changes in voltage level following a change in the heater control signal. The microcomputer 400 averages instantaneous values of the NOx concentration signal, as indicated by a1 and b1 picked up in the two adjacent power supply on-durations and instantaneous values, as indicated by a2 and b2, picked up in the two adjacent power supply off-durations to produce average values a3 and b3, respectively according to equations below.

$$a3=(a1+a2)/2$$

$$b3=(b1+b2)/2$$

The average values a3 and b3, as indicated by a broken line in FIG. 16(b), have the same value regardless of a change in duty cycle of the PWM signal.

The microcomputer 400 provides the correction signal indicative of the average values a3 and b3 to the correction circuit 450. The correction circuit 450 corrects the output of the NOx concentration determining circuit 410 by eliminating a difference between the output of the NOx concentration determining circuit 410 and the correction signal (i.e., the average values a3 and b3) to produce the error-corrected NOx concentration signal.

The apparatus of this embodiment also monitors the correction signal produced in the microcomputer 400 to measure a shift between the value of the error-corrected NOx concentration signal and the true value of the concentration of NOx caused by the time sequential on-off control of power supply to the heater 103 and adjusts a gain of the NOx concentration determining circuit 410 so as to eliminate the shift. This solves a problem that the adjustment of gain of the NOx concentration determining circuit 410 using an output of the NOx concentration determining circuit 410 during the PWM control will result in a variation in the gain depending upon the duty cycle of the heater control signal.

The apparatus of this embodiment is, as described above, designed to perform the on-off control of power supply to the heater 103 at a relatively low frequency (several Hz to several tens Hz), similar to the conventional gas concentration measuring apparatuses, thus eliminating the need for sample-and-hold circuits, as employed in FIG. 14, as well as expensive A/D converters.

The fifth embodiment of the invention will be described below.

The leakage current resulting from a change in resistance of the insulating layer 104 of the gas concentration sensor 100 changes with a change in voltage of a power supply (i.e., a battery mounted in the vehicle) for the heater 103 and a change in temperature of each of the pump cell 110 and the sensor cell 120. The voltage of the power supply changes greatly within a range of +B to ground potential (e.g., from 10 to 16V), which will change the degree of influence of the leakage current on an output of the gas concentration sensor 100. Additionally, the temperature of each of the pump cell 110 and the sensor cell 120 changes with a change in temperature of exhaust gasses to be measured by the gas concentration sensor 100, which will also change the degree of influence of the leakage current on the output of the gas concentration sensor 100. In order to avoid this problem, the gas concentration measuring apparatus of the fifth embodiment is designed to estimate the degree of influence of the leakage current on the outputs of the gas concentration sensor 100 during the on-off control of supply of power to the heater 103 and correct the output of the gas concentration sensor 100 so as to compensate for an error produced by the leakage current flowing into the gas concentration sensor 100.

Figure 17:
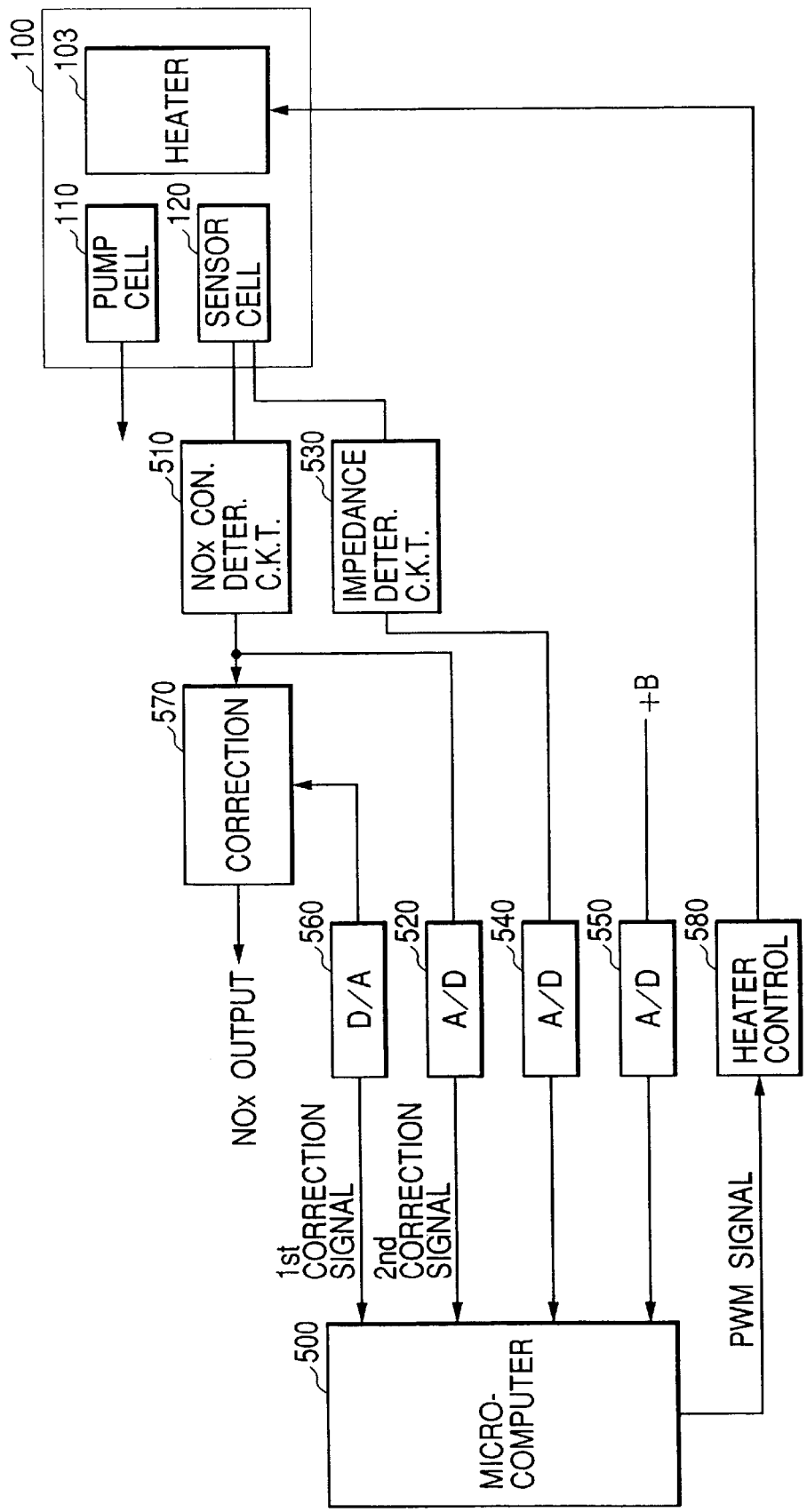
FIG. 17 is a block diagram which shows a gas concentration measuring apparatus according to the fifth embodiment of the invention.

FIG. 17 shows the gas concentration measuring apparatus according to the fifth embodiment of the invention.

The microcomputer 500 provides a PWM signal of a several Hz to several tens Hz (e.g., 7.8 Hz) to the heater control circuit 580. The heater control circuit 580 performs, like the above embodiments, the on-off control of supply of power to the heater 103 of the gas concentration sensor 100. The NOx concentration determining circuit 510 converts the NOx current flowing through the sensor cell 120 into a voltage signal indicating the concentration of NOx and outputs it to the correction circuit 570 and the microcomputer 500 through the A/D converter 520.

The impedance measuring circuit 530, like the one shown in FIG. 1, measures the impedance of the sensor cell 120 and provides a signal indicative thereof to the microcomputer 500 through the A/D converter 540. The battery voltage +B (i.e., the voltage of a power supply for the heater 103) is inputted to the microcomputer 500 through the A/D converter 550.

Figure 18A:
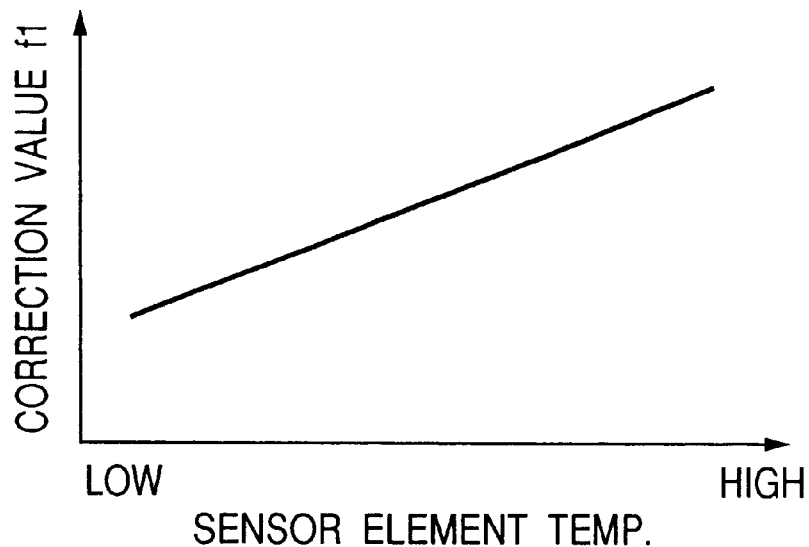
FIG. 18(a) shows a relation between a correction value f1 and the sensor element temperature.
Figure 18B:
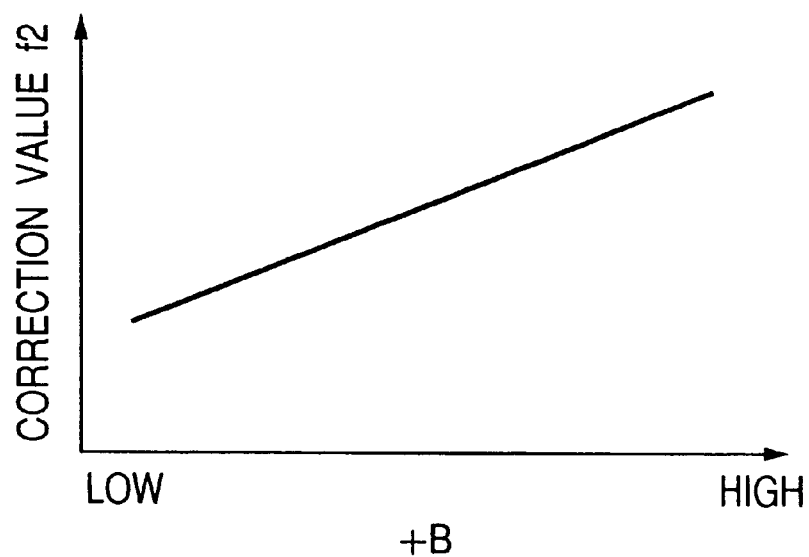
FIG. 18(b) shows a relation between a correction value f2 and the voltage of a power supply for a heater.

The microcomputer 500, like the fourth embodiment, averages the outputs of the NOx concentration determining circuit 510 provided both in the power supply on- and off-durations to produce a first correction signal based on the average value and outputs it to the correction circuit 570 through the D/A converter 560. The microcomputer 500 converts the impedance of the sensor cell 120 measured by the impedance measuring circuit 530 into the temperature of the sensor cell 120 to determine a correction value f1 based on the temperature of the sensor cell 120 and also determines a correction value f2 based on the battery voltage +B inputted through the A/D converter 550. For instance, the correction values f1 and f2 are determined by look-up using maps, as shown in FIGS. 18(a) and 18(b). The microcomputer 500 produces a second correction signal based on the correction values f1 and f2 and outputs it to the correction circuit 570 through the D/A converter 560.

The correction value f1 is so determined as to compensate for an error contained in an output of the NOx concentration determining circuit 510 arising from a change in the leakage current flowing into the gas concentration sensor 100 during the on-off control of supply of power to the heater 103 caused by a change in temperature of the sensor cell 120 and increases as the temperature of the sensor cell 120 increases. Similarly, the correction value f2 is so determined as to compensate for an error contained in the output of the NOx concentration determining circuit 510 arising from a change in the leakage current during the on-off control of supply of power to the heater 103 caused by a change in battery voltage +B and increases as the battery voltage +B increases. Instead of the battery voltage +B, the voltage developed across the terminals of the heater 103 may be used. The second correction signal may alternatively be produced using either of the first and second correction values f1 and f2.

The correction circuit 570 uses the first and second correction signals to correct errors contained in the NOx concentration signal inputted from the NOx concentration determining circuit 410 arising from the changes in leakage current caused by the on-off control of the supply of power to the heater 103 and the changes in temperature of the sensor cell 120 and battery voltage +B.

FIGS. 19(a), 19(b), 19(c), and 19(d) are time charts which show the heater control signal used in the on-off control of supply of power to the heater 103, the NOx concentration signal inputted to the microcomputer 500 from the NOx concentration determining circuit 510, the averaged NOx concentration signal, and the eror-corrected NOx concentration signal outputted from the correction circuit 570, respectively.

Figure 19A:
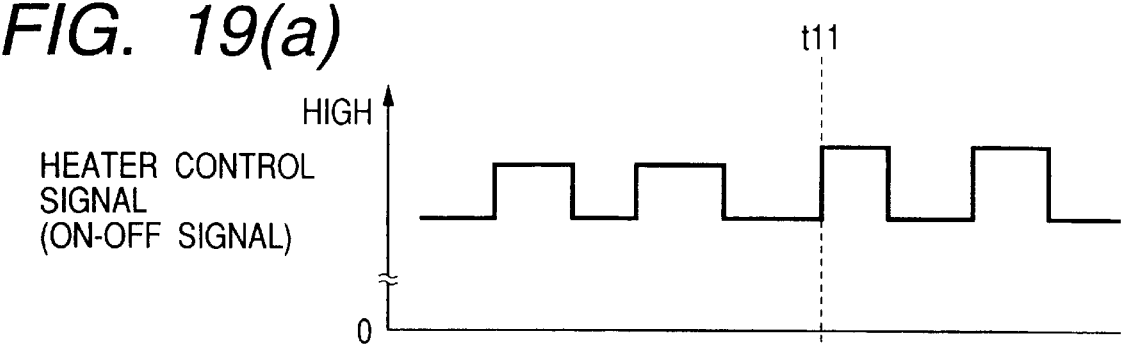
FIG. 19(a) shows a heater control signal.
Figure 19B:
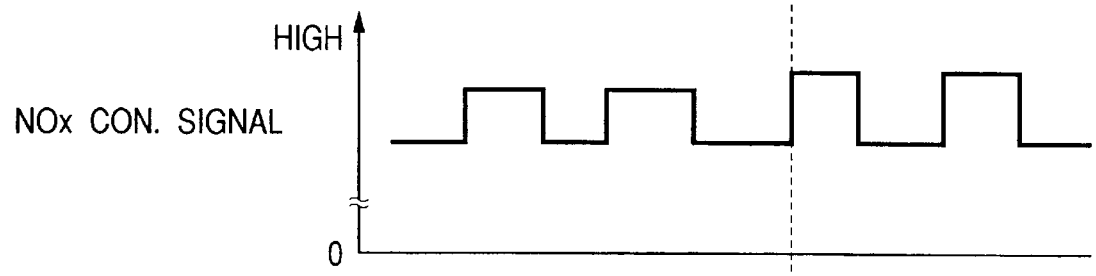
FIG. 19(b) shows a NOx concentration signal.
Figure 19C:
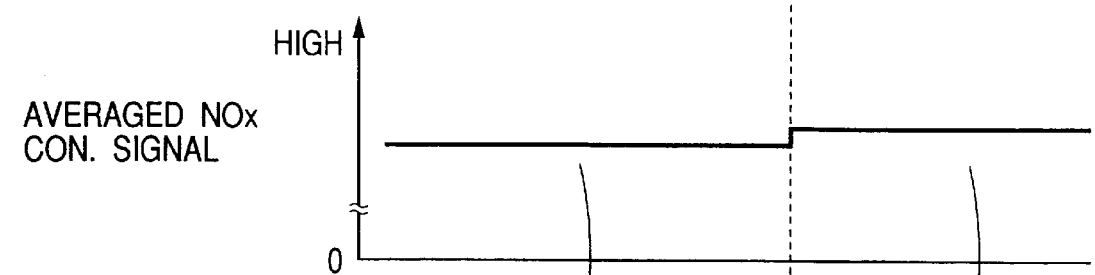
FIG. 19(c) shows an averaged NOx concentration signal.
Figure 19D:
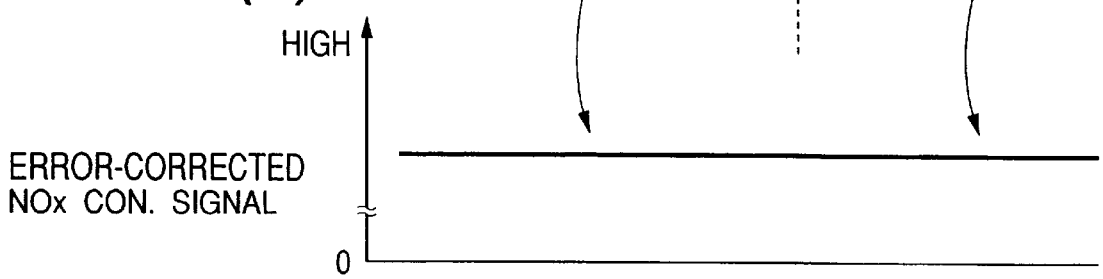
FIG. 19(d) shows an error-corrected NOx concentration signal.

At time t11, the battery voltage +B increases. The concentration of NOx is constant. The error contained in the NOx concentration signal caused by the on-off control of supply of power to the heater 103 is, as can be seen from FIG. 19(c), corrected by the first correction signal provided by the microcomputer 500. After time t1, the error-corrected signal in FIG. 19(c) is increased with the increase in battery voltage +B, but this increase is, as shown in FIG. 19(d), compensated for by the second correction signal.

The degree of influence of the leakage current on the output of the NOx concentration determining circuit 510 during the power supply off-duration depends upon whether the heater control circuit 580 has the high side switch or low side switch structure. It is, thus, advisable that the output of the NOx concentration determining circuit 510 be corrected in each of the power supply on- and off-durations. Specifically, in the case where the heater control circuit 580 has the low side switch structure, in the power supply off-duration, a minus terminal (−) of the heater 103 is opened, while a plus terminal (+) of the heater 103 is kept connected to the battery (+B). Alternatively, in the case of the high side switch structure, the plus terminal (+) is opened, while the minus terminal (−) is kept connected to ground. The leakage current flowing to the gas concentration sensor 100 in the power supply off-duration is, thus, changed depending upon whether the heater 103 is kept connected to the battery or ground. Accordingly, this change in leakage current is preferably considered in correcting the output of the NOx concentration determining circuit 510.

The both terminals of the heater 103 may alternatively be kept opened in the power supply off-duration. In this case, it is advisable that only a change in battery voltage +B be considered in correcting the output of the NOx concentration determining circuit 510.

A gas concentration measuring apparatus according to the sixth embodiment will be described below with reference to FIGS. 20(a) to 22(b).

Figure 20A:
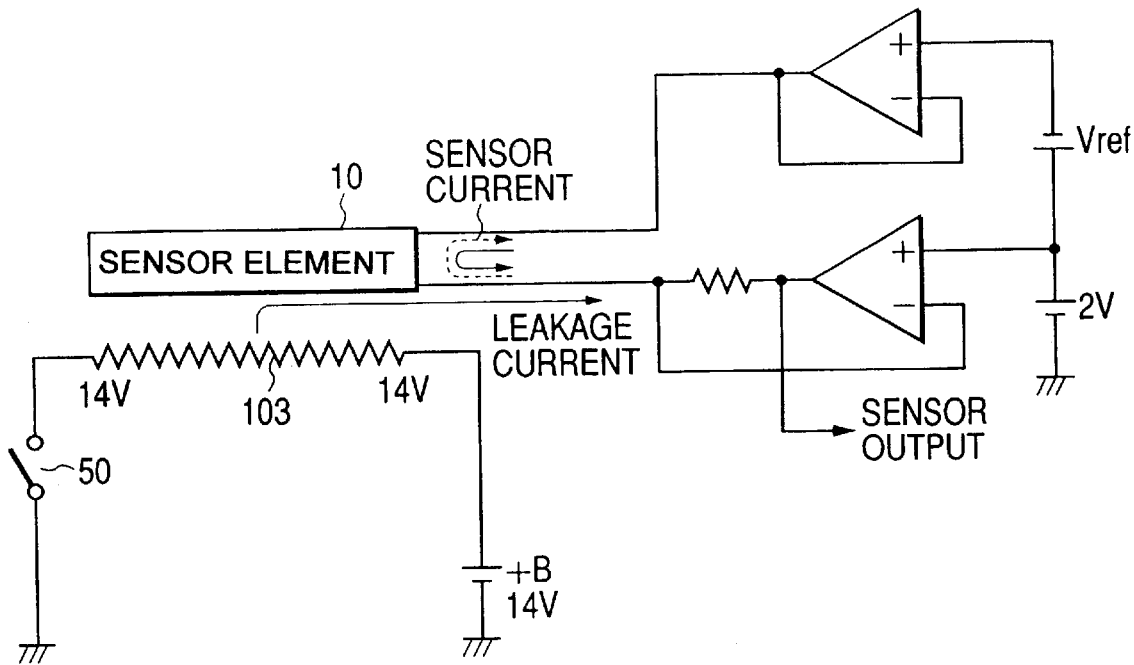
FIGS. 20(a) and 20(b) are block diagrams which show a comparative example of a gas concentration measuring apparatus.
Figure 20B:
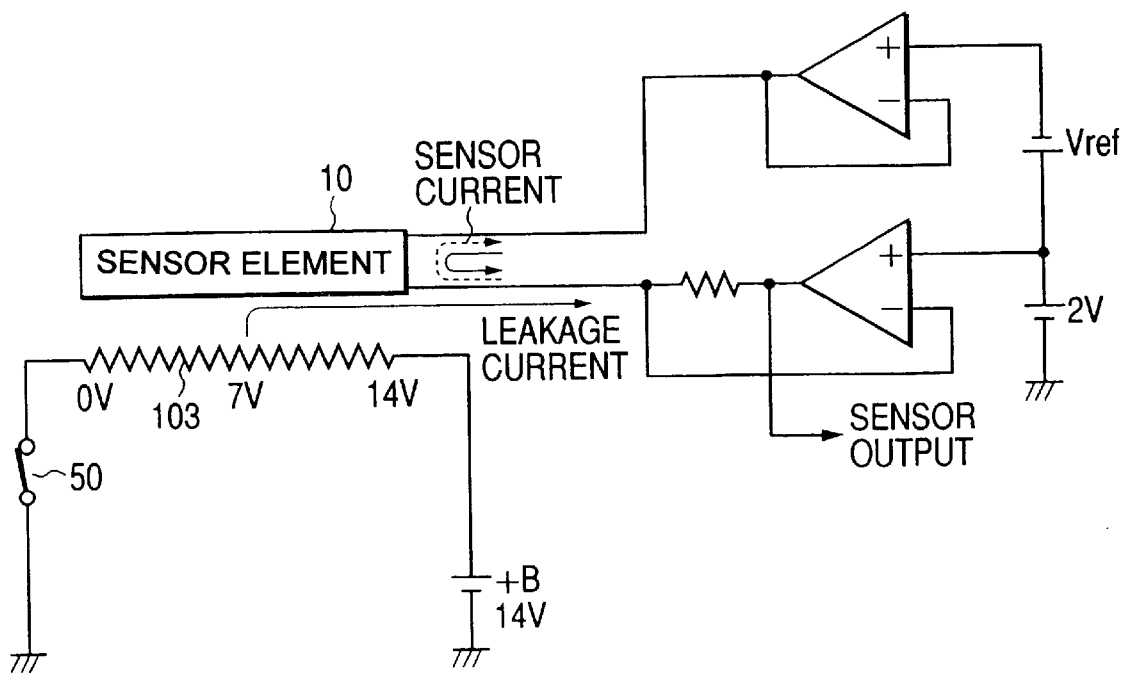

FIGS. 20(a) and 20(b) show a comparative example as illustrated simply for convenience of disclosure.

The heater 103 heats the sensor element 10 and connects at one end to a power supply (+B) and at the other end to ground through a switch 50. The switch 50 is turned on and off cyclically under the same on-off control as described above to supply the power to the heater 103. In a case where the gas concentration measuring apparatus is mounted in an automobile, the heater 103 is connected to a 14V storage battery. The reference voltage Vref (e.g., 2V) is applied to the sensor element 10. The output of the sensor element 10 is picked up by an microcomputer through an A/D converter and thus is a signal of 0 to 5V. When the switch 50 is, as shown in FIG. 20(a), opened, the voltage developed across the ends of the heater 103 will be 14V. Alternatively, when the switch 50 is, as shown in FIG. 20(b), closed, the voltage applied to the heater 103 varies within a range of 0 to 14V. Therefore, it is appreciated that a difference between the voltage applied to the heater 103 and the voltage of the sensor output becomes great when the switch 50 is opened, thereby resulting in an increase in leakage current flowing into the sensor element 10.

Figure 21A:
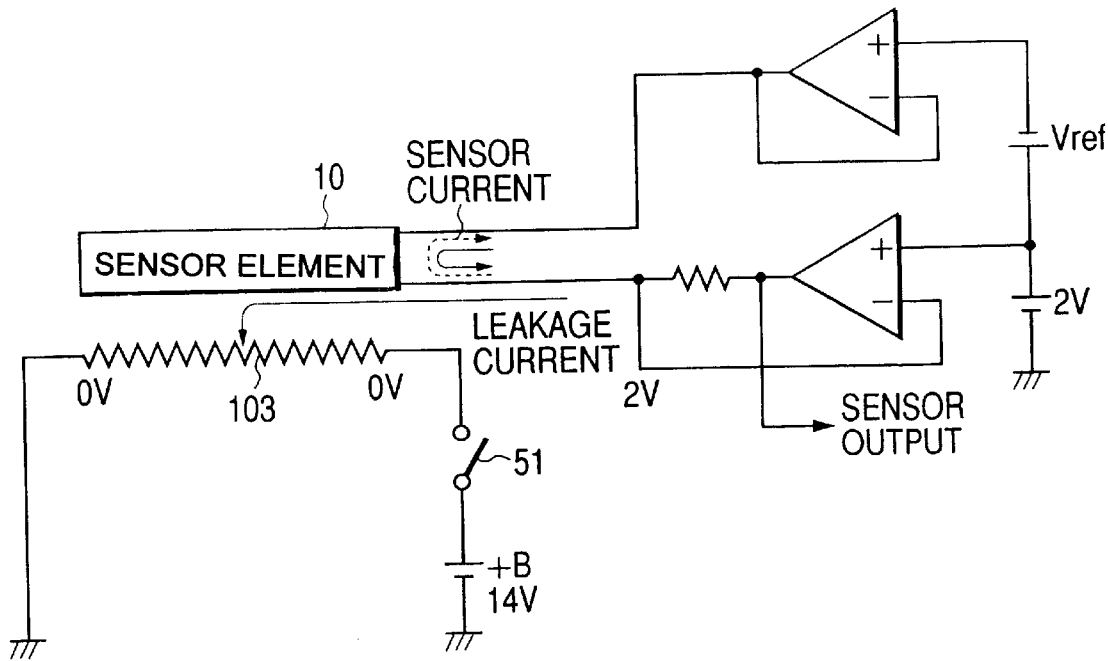
FIGS. 21(a) and 21(b) are block diagrams which show a gas concentration measuring apparatus according to the sixth embodiment of the invention.
Figure 21B:
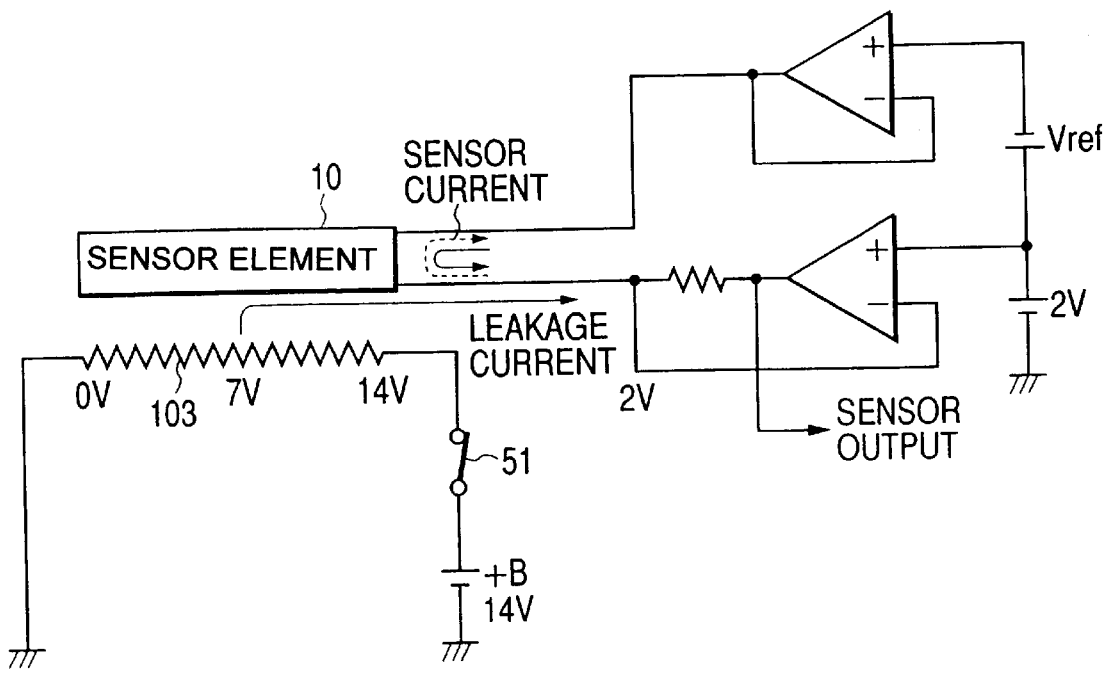

In order to avoid such a problem, the gas concentration measuring apparatus of the sixth embodiment, as shown in FIGS. 21(a) and 21(b), has the switch 51 disposed between the power source and the heater 103. The switch 51 may be made of a transistor. The sensor element 10 consists of the pump cell 110 and/or the sensor cell 120. The power is, like the above embodiments, supplied to the heater 103 cyclically in the on-off control. When the power is supplied to the heater 103, the switch 51 is, as shown in FIG. 21(b), closed. Alternatively, when the supply of power to the heater 103 is cut, the switch 51 is, as shown in FIG. 21(a), opened to block the communication between the heater 103 and the power supply, thereby causing a voltage of zero (0) to appear across the heater 103, which minimizes an error component contained in the output of the sensor element 10 arising from the leakage current.

Figure 22A:
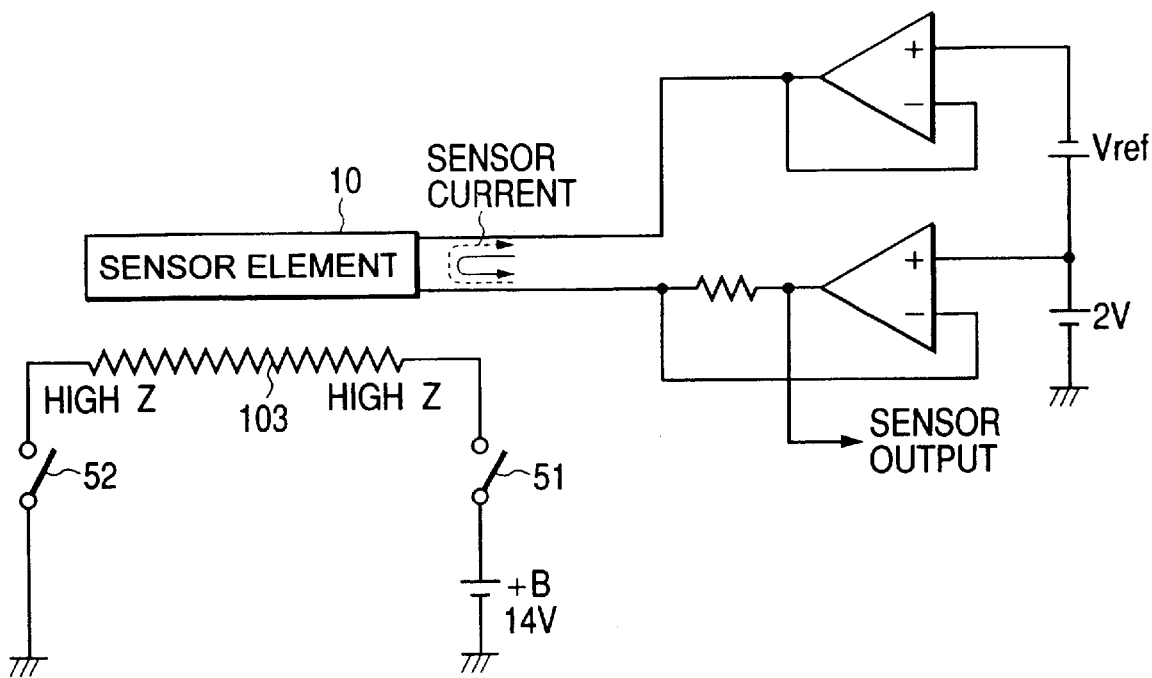
FIGS. 22(a) and 22(b) are block diagrams which show a modification of the gas concentration measuring apparatus shown in FIGS. 21(a) and 21(b).
Figure 22B:
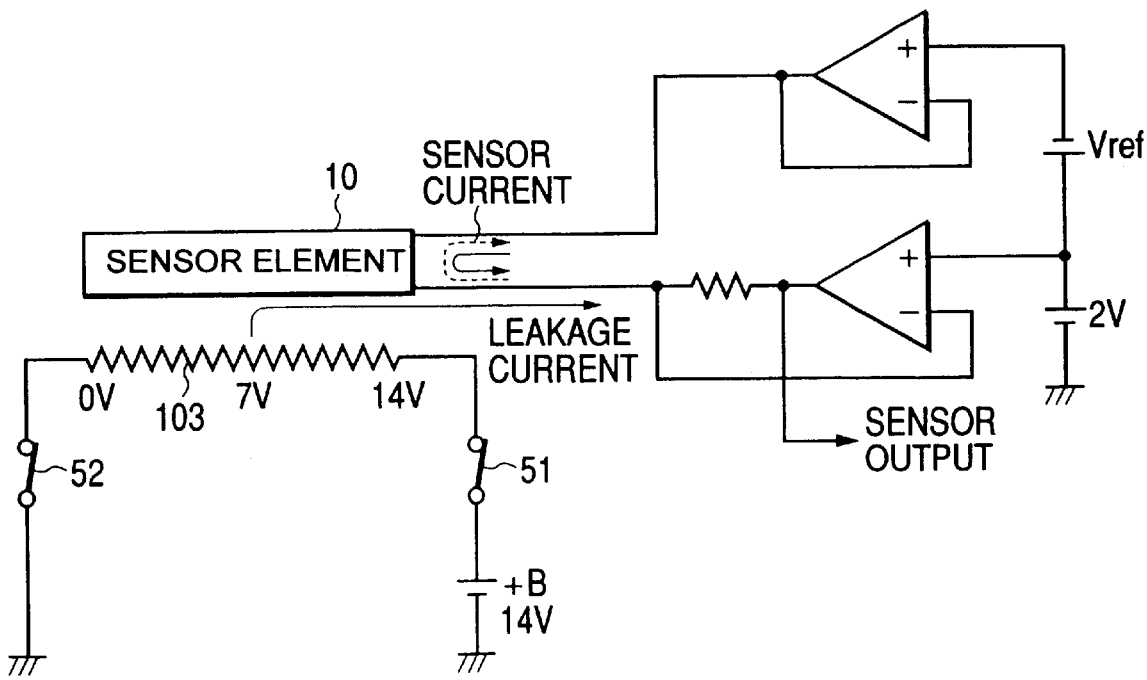

The switch 52, as shown in FIGS. 22(a) and 22(b) may also be disposed between the heater 103 and ground. When the power is supplied to the heater 103, the switches 51 and 52 are, as shown in FIG. 22(b), closed. Alternatively, when the supply of power to the heater 103 is cut, the switches 51 and 52 are, as shown in FIG. 22(a), opened, thereby bringing a potential difference between the ends of the heater 103 into zero (0), which minimizes an error component contained in the output of the sensor element 10.

Modifications of the above embodiments will be described below.

The voltage control circuit 220 in the first embodiment is made of the switching power supply as shown in FIG. 6, but may use a series power supply. A combination of a series power supply and a switching power supply may alternatively be used as it has the structure in which a change in voltage applied to the heater 103 is small.

The second embodiment, as shown in FIG. 9, measures the concentrations of $O_2$ and NOx through the $O_2$ concentration determining circuit 310 and the NOx concentration determining circuit 320 separately, however, may alternatively be designed to input outputs of the $O_2$ concentration determining circuit 310 and the NOx concentration determining circuit 320 to a microcomputer through an A/D converter and perform a DPS operation to separate the input into components indicating the $O_2$ concentration and the NOx concentration. The low-pass filters 330 and 340 may be built in the $O_2$ concentration determining circuit 310 and the NOx concentration determining circuit 320 to perform a filtering operation in the course of amplification of weak currents picked up from the pump cell 110 and the sensor cell 120.

The fourth embodiment, as shown in FIG. 15, averages the outputs of the NOx concentration determining circuit 410 provided both in the power supply on- and off-durations to provide the correction signal to the correction circuit 450, however, may alternatively be designed to determine a correction value fa using an equation below and produce the correction signal based on the correction value fa.

$$fa=(\alpha \times a1+\beta \times a2)/(\alpha+\beta)$$

where $\alpha$ and $\beta$ are weighting coefficients determined as functions of the degrees of influence of the leakage current on the output of the NOx concentration determining circuit 410 in the power supply on- and off-durations. If the degree of influence of the leakage current in the power supply on-duration is greater than the other, $\alpha$ is set greater than $\beta$ ($\alpha>\beta$). If both may be considered to be equal to each other, $\alpha$ and $\beta$ of the same value are used.

The microcomputer 400 in the fourth embodiment may perform in itself the function of the correction circuit 450.

The fourth and fifth embodiments may also correct a signal indicative of the $O_2$ concentration the same manner as used in correcting the signal indicative of the NOx concentration.

A gas concentration sensor having more than two cells or a single cell which measures only the concentration of $O_2$ may be used in the above embodiments.

A gas concentration sensor having a structure other than a laminated structure, as shown in FIG. 2, may also be used in the above embodiments.

A gas concentration sensor which is designed to decompose and discharge $O_2$ contained in gasses to be measured through a pump cell and decompose HC or CO contained in the gasses after the decomposition of $O_2$ through a sensor cell may also be used in the above embodiments.

A gas concentration sensor which is designed to produce an electromotive force as a signal indicating the concentration of a specified component contained in gasses to be measured may also be used in the above embodiments. For instance, Japanese Patent First Publication No. 11-108888 discloses such a sensor, disclosure of which is incorporated herein by reference.

The gas concentration measuring apparatus may be designed to output to an external device the $O_2$ current and/or the NOx current either for the power supply-on duration in which the power is supplied to the heater 103 or for the power supply-off duration in which the supply of power to the heater 103 is cut for facilitating correction of the error contained in the $O_2$ current and/or the NOx current arising from the leakage current in the external device. The output to the external device may be achieved using, for example, a sample-and-hold circuit. Since the apparatus is designed to output the sensor signal either for the power supply-on duration or for the power supply-off duration, it is insensitive to a fine change in behavior of the sensor 100, but has a simple structure. It is, however, possible to make the apparatus sensitive to the fine change in behavior of the sensor 100 by increasing the frequency of control of the heater 103 to increase the number of samples in the sample-and-hold circuit.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas concentration measuring apparatus comprising:
   a gas concentration sensor including a sensor element producing a signal indicative of the concentration of a preselected component contained in gasses, a heater heating the sensor element, and an insulator disposed between the sensor element and the heater;
   a heater control circuit controlling a supply of power to the heater of said gas concentration sensor; and
   an error correcting circuit correcting an error contained in the signal produced by the sensor element of said gas concentration sensor arising from a leakage current flowing into the sensor element through the insulator during control of the supply of power to the heater by said heater control circuit.

2. A gas concentration measuring apparatus as set forth in claim 1, wherein said heater control circuit determines a target voltage to be applied to the heater for keeping a temperature of the sensor element of said gas concentration sensor at a given value required for activation of the sensor element and controls the supply of power to the heater based on the target voltage.

3. A gas concentration measuring apparatus as set forth in claim 1, wherein said heater control circuit limits a change in voltage applied to the heater when the gas concentration sensor is in a activated state to below a given value.

4. A gas concentration measuring apparatus as set forth in claim 3, wherein said heater control circuit includes, a power supply, a switching element, a coil, and a capacitor, the switching element being turned on and off to apply a voltage of the power supply to the heater cyclically, the coil and the capacitor serving to smooth the voltage of the power supply.

5. A gas concentration measuring apparatus as set forth in claim 4, wherein a switching frequency of the switching element is 1 kHz or more.

6. A gas concentration measuring apparatus as set forth in claim 4, wherein a switching frequency of the switching element is at least greater than or equal to a frequency of a change in signal outputted from said gas concentration sensor.

7. A gas concentration measuring apparatus as set forth in claim 4, further comprising a filter which cuts off low frequency components below 100 Hz from the signal produced by the sensor element of said gas concentration sensor.

8. A gas concentration measuring apparatus as set forth in claim 5, further comprising a filter which cuts off low frequency components below at least the switching frequency from the signal produced by the sensor element of said gas concentration sensor.

9. A gas concentration measuring apparatus as set forth in claim 1, wherein the sensor element includes a first cell which is responsive to application of voltage to discharge oxygen contained in the gasses and produces a current signal as a function of a concentration of the oxygen and a second cell which is responsive to application of voltage to produce a current signal as a function of a concentration of a given gas component contained in the gasses after the oxygen is discharged through the first cell.

10. A gas concentration measuring apparatus as set forth in claim 1, wherein the sensor element has a cell which produces an electromotive force as the gas concentration signal.

11. A gas concentration measuring apparatus comprising:
a gas concentration sensor including a sensor element producing a signal indicative of the concentration of a preselected component contained in gasses, a heater heating the sensor element, and an insulator disposed between the sensor element and the heater;
a heater control circuit supplying power to the heater cyclically using a pulse-width modulated (PWM) signal; and
a filter passing frequency components of the signal produced by the sensor element within a given low frequency band,
wherein a frequency of the PWM signal is so determined as to allow said filter to compensate for an error which is contained in the signal inputted to said filter and which arises from the PWM signal.

12. A gas concentration measuring apparatus as set forth in claim 11, wherein the frequency of the PWM signal is ten or more times a cutoff frequency of said filter.

13. A gas concentration measuring apparatus as set forth in claim 11, wherein the frequency of the PWM signal is at least greater than a frequency of a change in signal outputted from said gas concentration sensor.

14. A gas concentration measuring apparatus as set forth in claim 12, wherein the cutoff frequency of said filter is less than or equal to 100 Hz.

15. A gas concentration measuring apparatus as set forth in claim 11, wherein the cutoff frequency of said filter is at least less than or equal to the frequency of the PWM signal.

16. A gas concentration measuring apparatus as set forth in claim 11, further comprising a detecting circuit which detects at least one of a voltage applied to the heater and a current flowing through the heater and a sample-and-hold circuit connected to an output of said detecting circuit.

17. A gas concentration measuring apparatus as set forth in claim 11, wherein the sensor element includes a first cell which is responsive to application of voltage to discharge oxygen contained in the gasses and produces a current signal as a function of a concentration of the oxygen and a second cell which is responsive to application of voltage to produce a current signal as a function of a concentration of a given gas component contained in the gasses after the oxygen is discharged through the first cell.

18. A gas concentration measuring apparatus as set forth in claim 11, wherein the sensor element has a cell which produces an electromotive force as the gas concentration signal.

19. A gas concentration measuring apparatus comprising:
a gas concentration sensor including a sensor element producing a gas concentration signal indicative of the concentration of a preselected component contained gasses, a heater heating the sensor element, and an insulator disposed between the sensor element and the heater;
a heater control circuit supplying power to the heater cyclically using a pulse-width modulated, (PWM) signal; and
a correction circuit monitoring values of the gas concentration signal in a power supply-on duration for which the power is supplied to the heater and a power supply-off duration for which supply of the power to the heater is cut off, said correction circuit corrects the gas concentration signal using the monitored values.

20. A gas concentration measuring apparatus as set forth in claim 19, wherein said correction circuit averages the values of the gas concentration signal in the power supply-on duration and the power supply-off duration and corrects the gas concentration signal using an averaged value.

21. A gas concentration measuring apparatus as set forth in claim 19, wherein the sensor element include a first cell which is responsive to application of voltage to discharge oxygen contained in the gasses and produces a current signal as a function of a concentration of the oxygen and a second cell which is responsive to application of voltage to produce a current signal as a function of a concentration of a given gas component contained in the gasses after the oxygen is discharged through the first cell.

22. A gas concentration measuring apparatus as set forth in claim 19, wherein the sensor element has a cell which produces an electromotive force as the gas concentration signal.

23. A gas concentration measuring apparatus comprising:
a gas concentration sensor including a sensor element producing a gas concentration signal indicative of the concentration of a preselected component contained in gasses, a heater heating the sensor element, and an insulator disposed between the sensor element and the heater;
a heater control circuit supplying power to the heater cyclically using a pulse-width modulated (PWM) signal; and
a correction circuit estimating an error which is to be contained in the gas concentration signal and which arises from a leakage current flowing into the sensor element through the insulator caused by a change in resistance of the insulator produced during control of supply of the power to the heater by said heater control circuit using the PWM signal, said correction circuit removing the estimated error from the gas concentration signal.

24. A gas concentration measuring apparatus as set forth in claim 23, wherein said correction circuit corrects the gas concentration signal using a greater correction value as a voltage of a power supply for the heater increases.

25. A gas concentration measuring apparatus as set forth in claim 23, wherein said correction circuit corrects the gas concentration signal using a greater correction value as a temperature of the sensor element increases.

26. A gas concentration measuring apparatus as set forth in claim 23, wherein the sensor element includes a first cell which is responsive to application of voltage to discharge oxygen contained in the gasses and produces a current signal as a function of a concentration of the oxygen and a second cell which is responsive to application of voltage to produce a current signal as a function of a concentration of a given gas component contained in the gasses after the oxygen is discharged through the first cell.

27. A gas concentration measuring apparatus as set forth in claim 23, wherein the sensor element has a cell which produces an electromotive force as the gas concentration signal.

* * * * *